(12) United States Patent
Wachter et al.

(10) Patent No.: US 7,353,829 B1
(45) Date of Patent: Apr. 8, 2008

(54) METHODS AND APPARATUS FOR MULTI-PHOTON PHOTO-ACTIVATION OF THERAPEUTIC AGENTS

(75) Inventors: Eric A. Wachter, Oak Ridge, TN (US); Walter G. Fisher, Knoxville, TN (US); John T. Smolik, Loudon, TN (US)

(73) Assignee: Provectus Devicetech, Inc., Knoxville, TN (US)

( * ) Notice: Subject to any disclaimer, the term of this patent is extended or adjusted under 35 U.S.C. 154(b) by 681 days.

(21) Appl. No.: 09/096,832

(22) Filed: Jun. 12, 1998

Related U.S. Application Data

(63) Continuation-in-part of application No. 08/739,801, filed on Oct. 30, 1996, now Pat. No. 5,829,448.

(51) Int. Cl.
*A61B 19/00* (2006.01)
*A61N 1/30* (2006.01)

(52) U.S. Cl. .......................... 128/898; 604/20
(58) Field of Classification Search ............. 607/88, 607/89, 92; 606/9, 13, 14; 604/20; 128/898
See application file for complete search history.

(56) References Cited

U.S. PATENT DOCUMENTS

| | | | | |
|---|---|---|---|---|
| 4,822,335 A | * | 4/1989 | Kawai et al. ............... | 604/20 |
| 4,973,848 A | * | 11/1990 | Kolobanov et al. ...... | 250/458.1 |
| 5,034,613 A | | 7/1991 | Denk et al. ............... | 250/458.1 |
| 5,050,597 A | * | 9/1991 | Daikuzono .................. | 128/395 |
| 5,089,384 A | | 2/1992 | Hale | |
| 5,217,455 A | * | 6/1993 | Tan .............................. | 606/9 |
| 5,268,862 A | | 12/1993 | Rentzepis | |
| 5,329,398 A | | 7/1994 | Lai et al. | |
| 5,445,608 A | * | 8/1995 | Chen et al. .................. | 604/20 |
| 5,469,454 A | | 11/1995 | Delfyett, Jr. | |
| 5,523,573 A | | 6/1996 | Hanninen et al. | |
| 5,541,947 A | | 7/1996 | Mourou et al. | |
| 5,571,152 A | * | 11/1996 | Chen et al. ................. | 607/92 |
| 5,586,981 A | | 12/1996 | Hu ................................ | 606/9 |
| 5,618,285 A | | 4/1997 | Zair ............................ | 606/10 |
| 5,656,186 A | | 8/1997 | Mourou et al. ......... | 219/121.69 |

(Continued)

OTHER PUBLICATIONS

Jean-Luc Boulnois, "Photophysical Processes in Recent Medical Laser Developments: A Review" Lasers in Med. Sci. vol. 1, pp. 47-66 (1986).
Anita M.R. Fisher, et al. "Clinical and Preclinical Photodynamic Therapy" Lasers in Surgery and Medicine 17:2-31, pp. 2-31 (1995).
Antony R. Young, "Photocarcinogenicity of Psoralens Used In Puva Treatment: Present Status In Mouse and Man" Journal of Photochem. and Photobiol. B: Biology, 6, pp. 237-247 (1990).
M.J. Wirth, et al. "Two-Photon Excited Molecular Fluorescence in Optically Dense Media" Analytical Chem. vol. 49, No. 13, pp. 2054-2057 (Nov. 1977).

(Continued)

*Primary Examiner*—Tom Barrett
(74) *Attorney, Agent, or Firm*—Cook, Alex, McFarron, Manzo, Cummings & Mehler, Ltd.

(57) ABSTRACT

A method and apparatus for the treatment of a particular volume of material, plant or animal tissue including the steps of treating the material plant or animal tissue with at least one photo-active agent, wherein the particular volume of the material, plant or animal tissue retains at least a portion of the at least one photo-active agent, and then treating the particular volume of the material plant or animal tissue with light sufficient to promote a multi-photon excitation of at least one of the at least one photo-active agent retained in the particular volume of the material, plant or animal tissue, wherein the at least one photo-active agent becomes active in the particular volume of the material, plant or animal tissue.

123 Claims, 15 Drawing Sheets
(1 of 15 Drawing Sheet(s) Filed in Color)

U.S. PATENT DOCUMENTS

| | | | |
|---|---|---|---|
| 5,674,698 | A | 10/1997 | Zarling et al. |
| 5,674,743 | A | 10/1997 | Ulmer |
| 5,689,519 | A | 11/1997 | Fermann et al. |
| 5,707,401 | A * | 1/1998 | Talmore ............ 607/88 |
| 5,720,894 | A | 2/1998 | Neev et al. ............ 216/65 |
| 5,759,767 | A | 6/1998 | Lakowicz et al. |
| 5,775,339 | A * | 7/1998 | Woodburn et al. ........ 128/898 |
| 5,815,262 | A | 9/1998 | Schrof et al. |
| 5,829,448 | A | 11/1998 | Fisher et al. ............ 128/898 |
| 5,898,720 | A | 4/1999 | Yamamoto et al. |
| 5,912,257 | A | 6/1999 | Prasad et al. |
| 5,952,818 | A | 9/1999 | Zhang et al. |
| 5,957,960 | A * | 9/1999 | Chen et al. ............ 607/92 |
| 6,099,522 | A | 8/2000 | Knopp et al. |
| 6,272,156 | B1 | 8/2001 | Reed et al. |

OTHER PUBLICATIONS

E.A. Wachter, Fisher et al. "Titanium: Sapphire Laser as an Excitation Source In Two-Photon Spectroscopy" Applied Spectroscopy, vol. 51, No. 2, pp. 218-226 (1997).
Sun-Yung Chen, et al. "Theory of two-photon induced fluorescence anisotropy decay in membranes" Biophys. J. Biophysical Society, vol. 64, pp. 1567-1575 (May 1993).
Joseph R. Lakowicz, et al. "Two-Color Two-Photon Excitation of Fluorescence" Photochemistry and Photobiology, pp. 632-635 (1996).
George C. Nieman, et al. "A new electronic state of ammonia observed by multiphoton ionization", J. Chem. Phys. 68 (12) pp. 5656-5657 (1978).
Philip M. Johnson, "The multiphoton ionization spectrum of benzene" Journal of Chemical Physics, vol. 64, No. 10, 4143-4148 (May 1976).
P.M. Johnson, et al. "The Discovery of a 3p Rydberg State in Benzene By Three-Photon Resonant Multiphoton Ionization Spectroscopy" Chemical Physics Letters, pp. 53-56 (1983).
S.G. Grubb, et al. "The three-photon spectrum of the $^1B_{2u}$-$^1A_{1g}$ transition in benzene: Analysis of vibronic and rotational structure" J. Chem. Phys. 81 (12) , American Institute of Physics, pp. 5255-5265 (1984).
J.R. Cable, et al. "A condensed phase study of the benzene $B_{2u}$-$^1A_{1g}$ three-photon transition" J. Chem. Phys. 85 (6), American Institute of Physics. pp. 3155-3164 (1986).
Philip M. Johnson, "The multiphoton ionization spectrum of trans-1,3 butadiene" Journal of Chem. Physics, vol. 64, No. 11, pp. 4638-4644 (1976).
Mark Seaver, et al. "Double Resonance Multiphoton Ionization Studies of High Rydberg States in NO", J. Phys. Chem, 1983, 87, pp. 2226-2231 American Chemical Society.
Bennett H. Rockney, et al. "Multiphoton ionization of nitrogen dioxide: Four photon spectroscopy of the $npo_u$ Rydberg series", J. Chem. Phys, vol. 78, No. 12, (1983).
Ruth McDiarmid, et al. "Four-photon Resonant Multiphoton Ionization Spectroscopy", Chemical Physics Letters vol. 76, No. 3, (1980).
D.L. Andrews, et al. "Polarization studies in multiphoton absorption spectroscopy", American Institute of Physics, J. Chem. Phys. 75(2), pp. 530-538 (1981).
Ignacy Gryczyniski, et al. "Fluorescence Spectral Properties of Troponin C Mutant F22W with One-, Two-, and Three-Photon Excitation", Biophysical Journal, vol. 71, pp. 3448-3453 (1996).
Joseph R. Lakowicz, et al. "Time-Resolved Fluorescence Spectroscopy and Imaging of DNA Labeled with DAPI and Hoechst 33342 Using Three-Photon Excitation", Biophysical Journal, vol. 72, pp. 567-578 (1997).
Ignacy Gryczynski, et al. "Rapid Communication—On the Possibility of Calcium Imaging Using INDO-1 With Three-Photon Excitation", Photochem. & Photobiology, vol. 62, No. 4, pp. 804-808 (1995).
Henryk Szmacinski, et al. "Three-Photon Induced Fluorescence of the Calcium Probe Indo-1", Biophysical Journal, vol. 70, pp. 547-555 (1996).
Guoqiang Xing, et al. "Modulation of resonant multiphoton ionization of $CH_3I$ by laser phase variation", American Institute of Physics, J. Chem. Phys. 104(3), pp. 826-831 (1996).
Xuebin Wang, et al. "Phase control of absorption in large polyatomic molecules" American Institute of Physics, J. Chem. Phys. 105(8), pp. 2992-2997 (1996).
Flam, "Laser Chemistry: The Light Choice", Science, vol. 266, pp. 215-217 (1994).
Christopher J. Bardeen, et al. "Feedback quantum control of molecular electronic population transfer", Chemical Physics Letters 280 (1997), pp. 151-158.
Service "Training Lasers to Be Chemists", Science, vol. 279, pp. 1847-1848 (1998).
Richard N. Zare "Laser Control of Chemical Reactions", Science, vol. 279, pp. 1875-1879 (1998).
David C. Clary, "Quantum Theory of Chemical Reaction Dynamics", Science, vol. 279, pp. 1879-1882 (1998).
Niels H. Damrauer, et al. "Femtosecond Dynamics of Excited-State Evolution in $[Ru(bpy)_3]^{2+}$", Science, vol. 275, pp. 54-57 (1997).
D. Zhong, et al. "Femtosecond Nucleophilic Substitution Reaction Dynamics" J. Am. Chem. Soc. 1997, 119 pp. 2305-2306.
W.G. Fisher, et al. Simultaneous Two-Photon Activation of Type-I Photodynamic Therapy Agents, Photochem. & Photobiol. 66(2), 1997 pp. 141-155.
Christopher R. Shea, et al. "Mechanistic Investigation of Doxycycline Photosensitization by Picosecond-pulsed and Continuous Wave Laser Irradiation of Cells in Culture", Journal of Biol. Chem. vol. 265, No. 11, pp. 5977-5982 (1990).
Dennis H. Oh, et al. "Two-Photon Excitation of 4'-Hydroxymethyl-4,5', 8-Trimethylpsoralen", Photochem. & Photobiol. 1997, 65(1), pp. 91-92.
S. Singh, et al. "Three-Photon Absorption in Napthalene Crystals by Laser Excitation", Physical Review Letters, vol. 12, pp. 612-614 (1964).
Iain D. Miller "An Introduction to Medical Lasers", Biophotonics International, Sep./Oct. 1997, pp. 50-51.
Kim S. Frederickson, et al. "Precise Ablation of Skin With Reduced Collateral Damge Using the Femtosecond-Pulsed, Terawatt Titanium-Sapphire Laser", Arch Dermatol, vol. 129, pp. 989-993 (1993).
Shinichi Watanabe, et al. "Comparative Studies of Femtosecond To Microsecond Laser Pulses on Selective Pigmented Cell Injury in Skin", Photochem. & Photobiol. vol. 53, No. 6, pp. 757-762 (1991).
David Stern, et al. "Corneal Ablation by Nanosecond, Picosecond, and Femtosecond Lasers at 532 and 625 nm", Arch Ophthalmol, vol. 107, pp. 587-592 (1989).
Daniel X. Hammer, et al. "Experimental Investigation of Ultrashort Pulse Laser-Induced Breakdwon Thresholds in Aqueous Media", IEEE Journal of Quantum Electronics, vol. 32, No. 4, pp. 670-678 (1996).
Reginald Birngruber, et al. "Femtosecond Laser-Tissue Interactions: Retinal Injury Studies", IEEE Journal of Quantum Electronics , vol. QE-23, No. 10, pp. 1836-1844 (1987).
Shear, J.B. et al, "Multiphoton-Excited Visible Emission by Serotonin Solutions," *Photochemistry and Photobiology*, vol. 65 No. 6, pp. 931-936, 1997.
International Search Report for application No. PCT/US99/12056, dated Sep. 13, 1999.
*The Photonics Dictionary 2000 Book 4.* 46th edition, 2000, pp. 5,6,77,105.
Niemz, *Laser-Tissue Interactions: Fundamentals and Application.* Springer-Verlag Berlin Heidelberg, 1996, pp. 45-147.

* cited by examiner

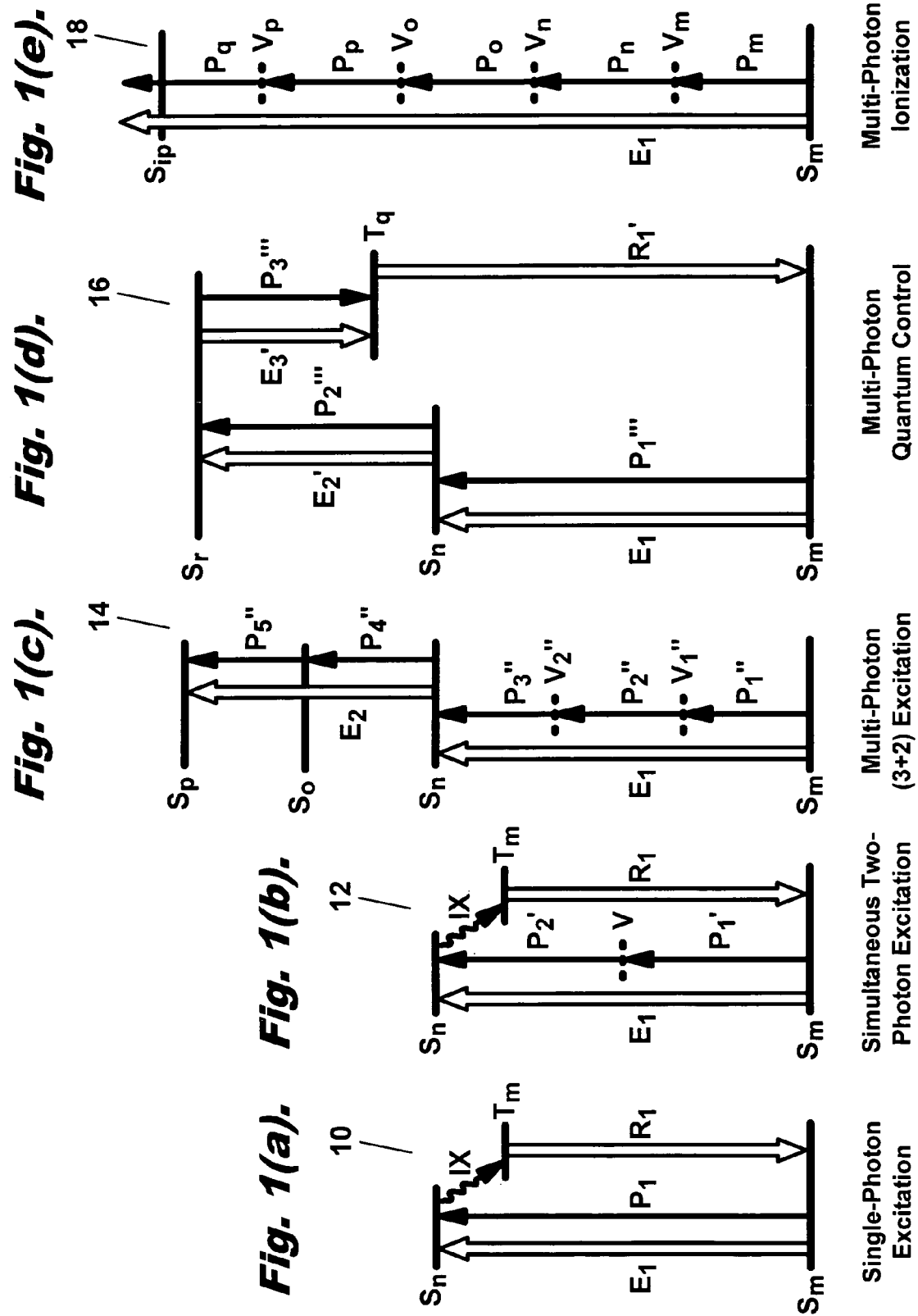

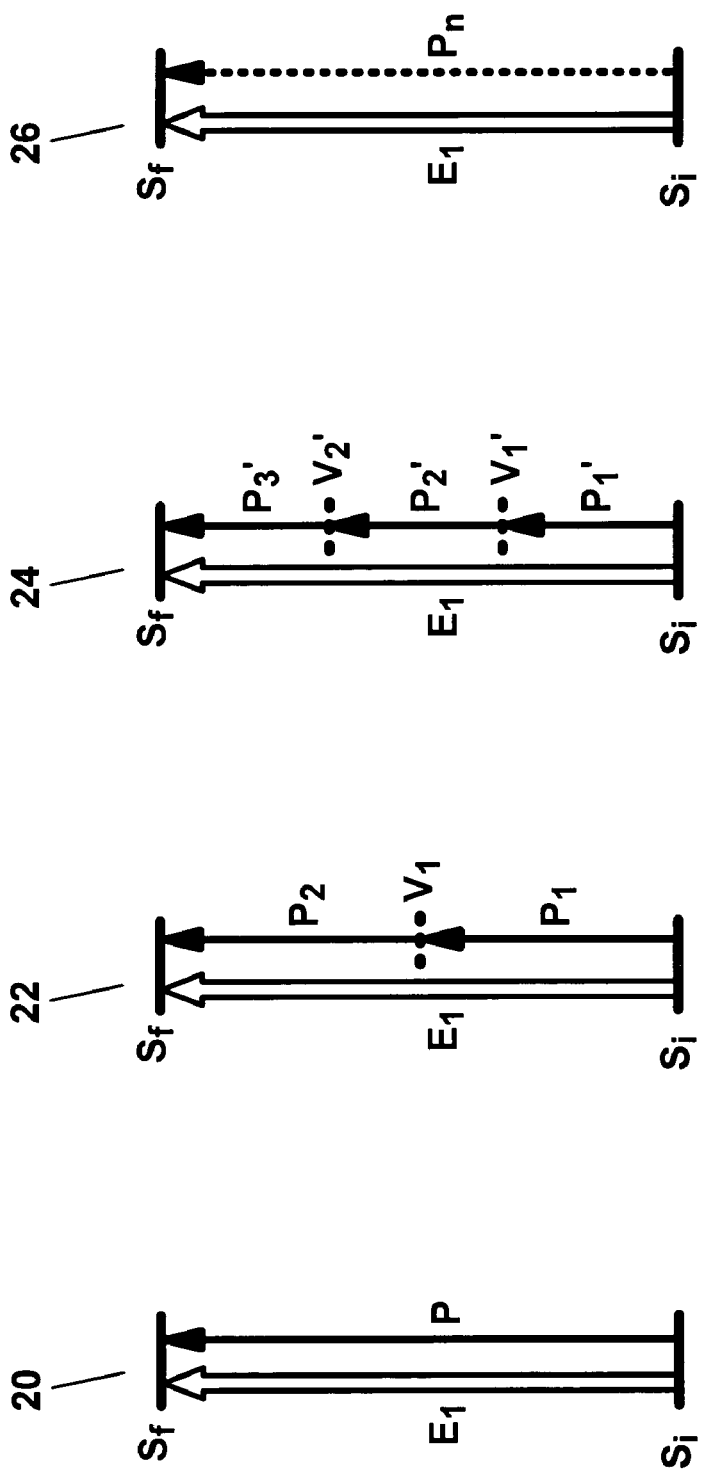

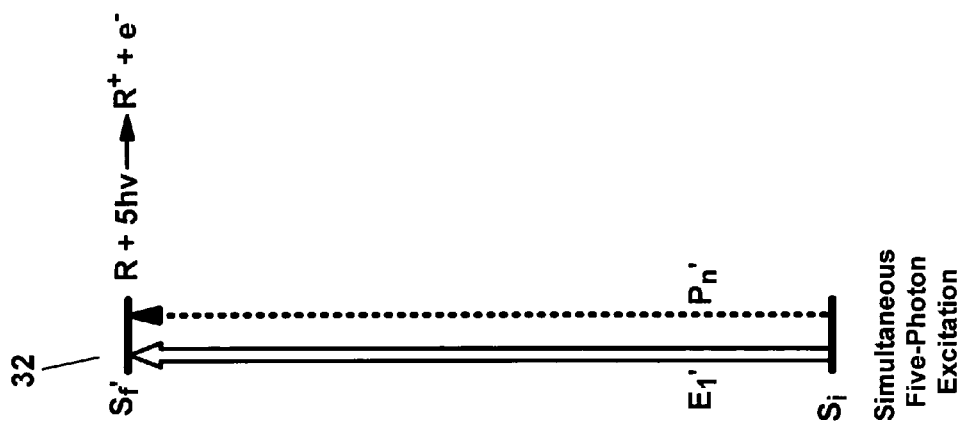
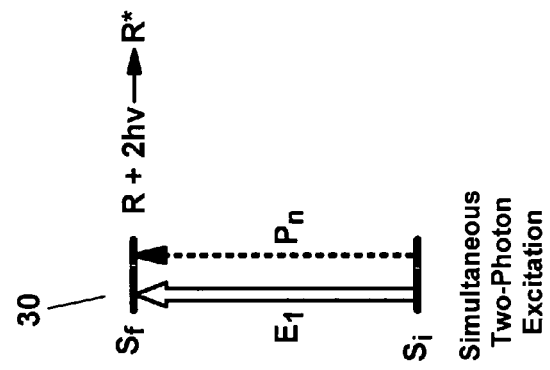

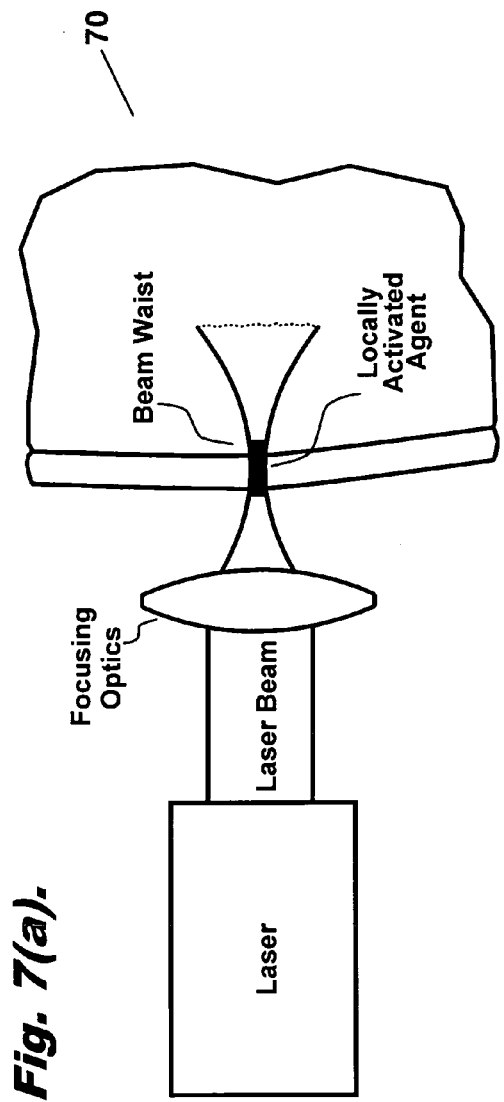
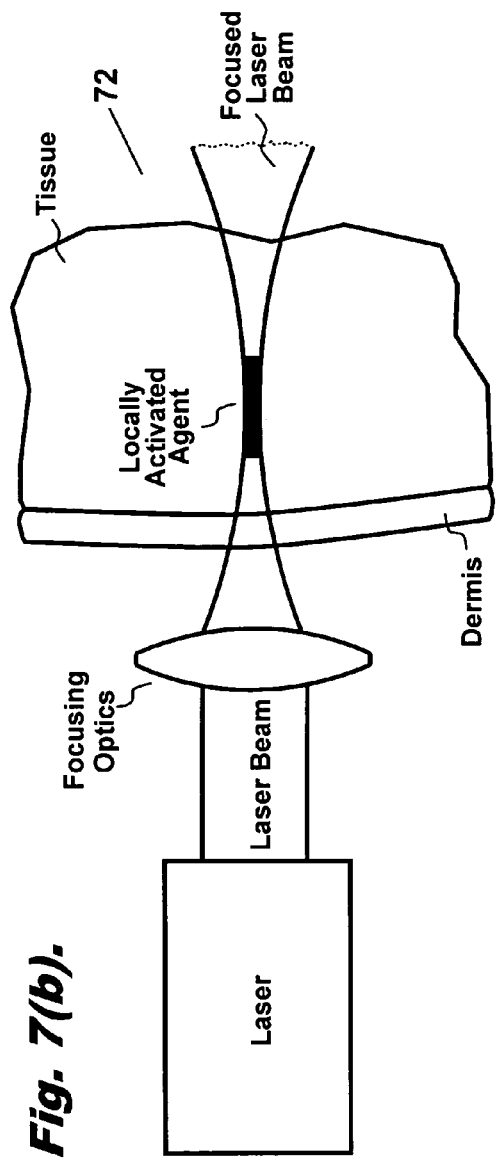
Fig. 7(a).
Fig. 7(b).

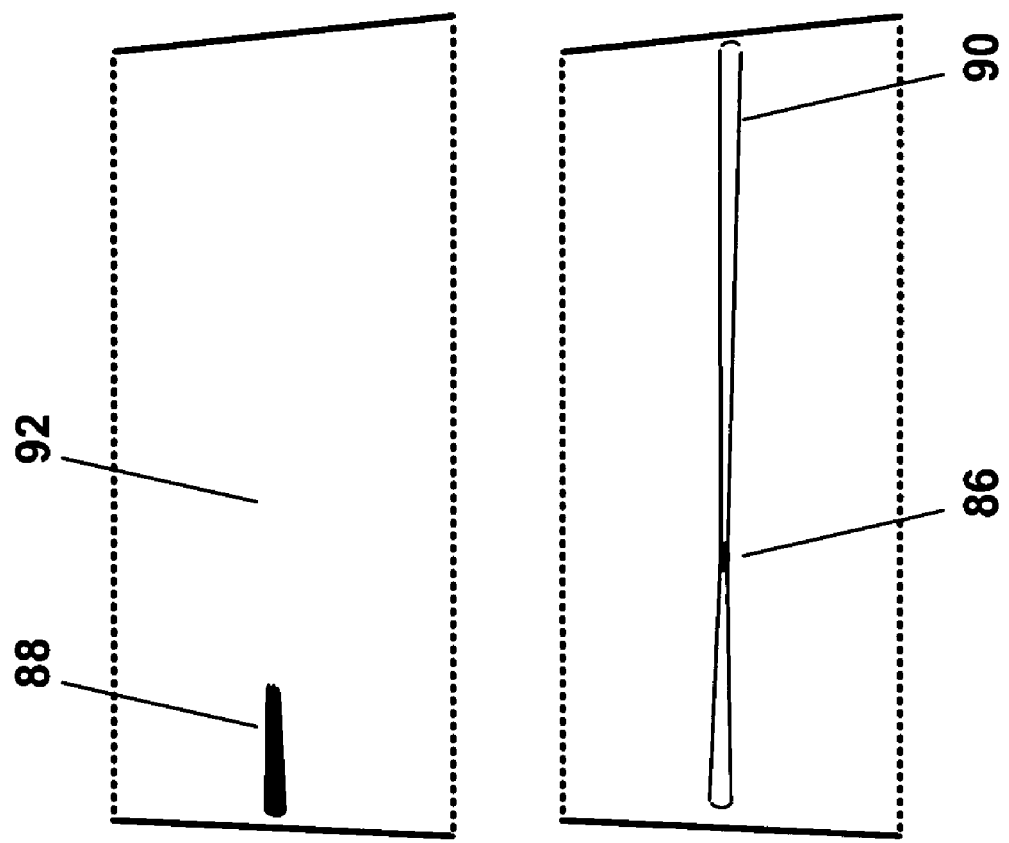
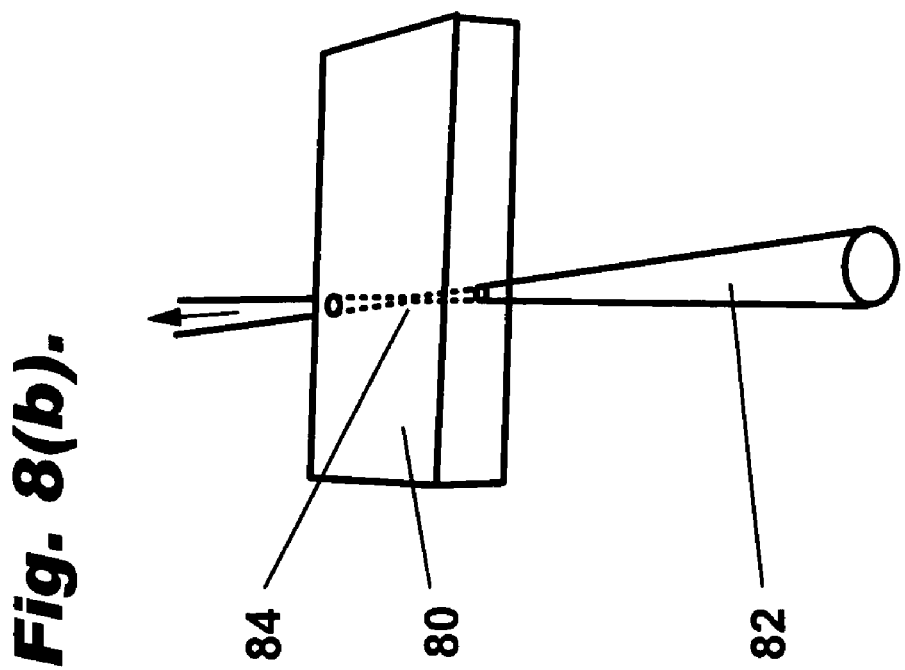
Fig. 8(b).

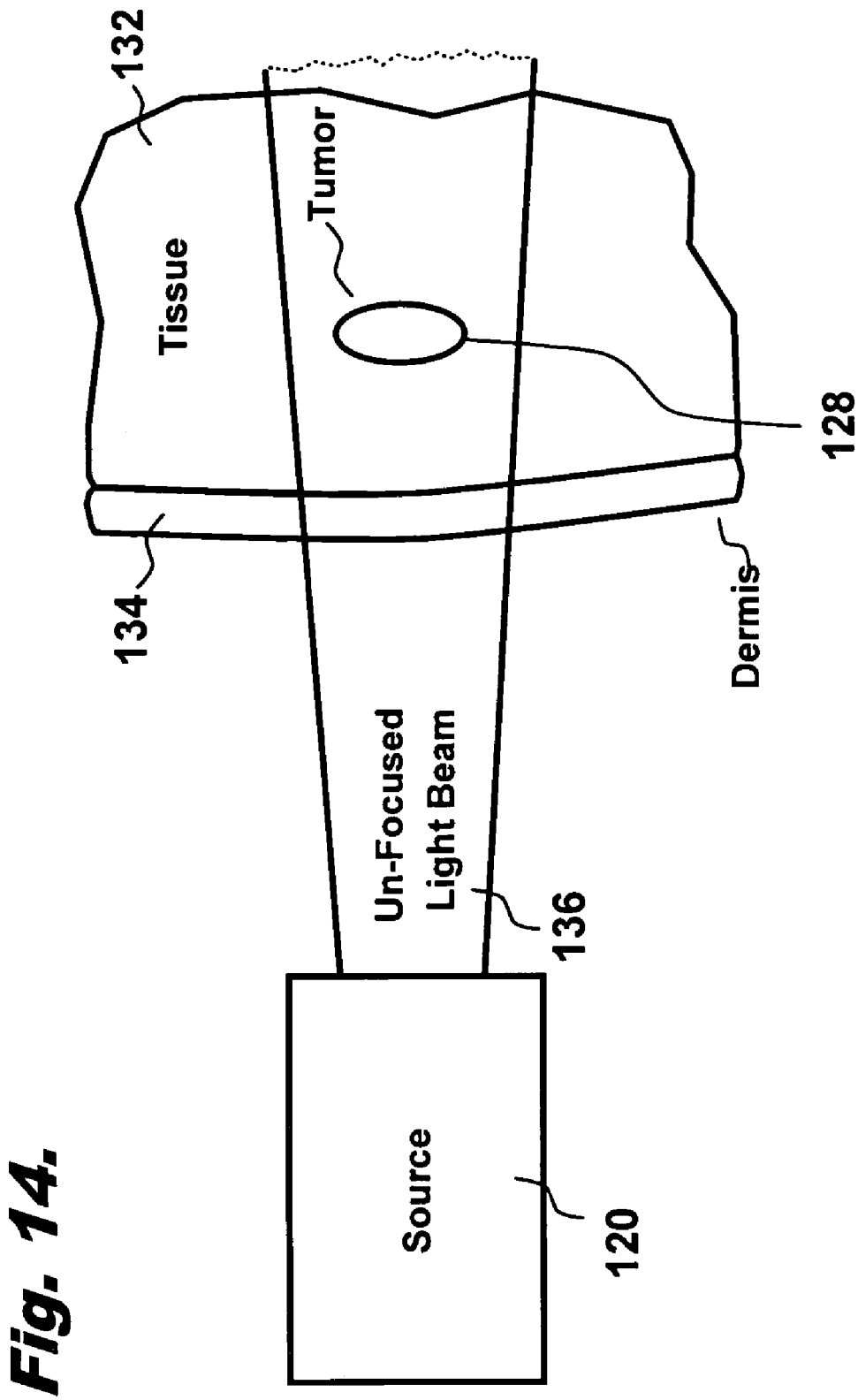

METHODS AND APPARATUS FOR MULTI-PHOTON PHOTO-ACTIVATION OF THERAPEUTIC AGENTS

CROSS REFERENCES TO RELATED MATERIALS

The present application is a continuation-in-part of U.S. patent application Ser. No. 08/739,801, filed on Oct. 30, 1996, now U.S. Pat. No. 5,829,448, issued on Nov. 3, 1998, entitled "Method for Improved Selectivity In Photo-Activation of Molecular Agents".

FIELD OF THE INVENTION

The present invention relates generally to methods and apparatus for achieving selective photo-activation of one or more therapeutic agents with a high degree of spatial control. The methods taught for achieving selective photo-activation utilize the special properties of non-linear optical excitation for promotion of an agent from one molecular energy state to another with a high degree of spatial and molecular specificity. The special features of these methods are applicable in the processing of various types of materials, and in particular afford distinct advantages in the treatment of disease in humans, and animals, and plants. Specifically, use of non-linear excitation methods facilitate controlled therapeutic activation of agents in tissue using light at visible to infrared wavelengths which is absorbed and scattered to a lesser extent than methods and optical radiations currently used.

BACKGROUND OF THE INVENTION

Flexible methods are needed in the medical field that allow selective activation of various molecular agents for a variety of therapeutic applications, including photodynamic therapy and localized surgical procedures. Desired improvements include enhancements in spatial or temporal control over the location and depth of activation, reduction in undesirable activation and damage to other co-located or proximal agents, tissues or structures, and increased preference in the activation of desired agents over that of other, non-targeted agents.

Since its discovery in the early 1960's, the laser has been anticipated as being capable of providing such selectivity and flexibility. For instance, various linear and non-linear photochemical and photophysical methods useful for harnessing the special capabilities of laser radiation have been developed that provide some improvements for some applications. A typical review of the many uses for lasers in medicine (see e.g. Miller, Biophotonics Intern. September/October (1997) 50–51; Boulnois, Lasers Med. Sci. 1 (1986) 47–66) demonstrates that lasers with optical outputs ranging from continuous wave (CW) to ultrashort pulsed beams and spanning wavelengths from the ultraviolet (UV) and visible to the near infrared (NIR) and infrared (IR) find useful application in medical treatments ranging from elimination of superficial skin disorders to delicate retinal surgery (e.g. Fisher et al., Lasers Surg. Med. 17 (1995) 2–31; Mourou et al., U.S. Pat. No. 5,656,186). Moreover, improved understanding of the non-specific damage properties of laser energy in various tissues (e.g. Hammer et al., IEEE J. Quant. Electron. 32 (1996) 670–678) has allowed practitioners to devise safer and more efficacious uses for the latest laser sources. However, in general, the performance and flexibility of current therapeutic laser methods is less than desired. Specifically, improved photo-activation methods are needed that may be used to selectively effect various therapeutic processes while providing improved performance and flexibility in the application of these processes.

Application of optical radiation to probe or transform molecular agents has been known for many years. For example, linear single-photon optical excitation has been used extensively for activation of molecular therapeutic agents in photodynamic therapy (PDT). (e.g. Fisher et al., Lasers Surg. Med. 17 (1995) 2–31). A generalized Jablonski diagram for such activation is shown in FIG. 1(a), wherein single-photon excitation (10) occurs when a photo-active agent is excited from a lower quantum-mechanically allowed state $S_m$ to a higher quantum-mechanically allowed state $S_n$ upon absorption of a certain energy $E_1$ which is provided by interaction of a single photon $P_1$ with the agent. Typically, intersystem crossing, IX, subsequently occurs to bring the excited agent to a long-lived activated state $T_m$ from which a photochemical reaction $R_1$ can occur. In the case of photodynamic therapy $R_1$ can include production of cytotoxic species, such as singlet oxygen. Unfortunately, performance of such excitation methods has not been as successful as desired. For example, there is strong evidence (see Young, J. Photochem. Photobiol. B, 6 (1990) 237–247) that the optical radiation $P_1$ used in some common treatment regimes can itself produce disease and other undesirable side effects. Furthermore, a less than desirable penetration depth has plagued most efforts at linear optical excitation of molecular therapeutic agents, primarily as a consequence of the effect of optical scatter and absorbance of the UV or visible activating optical radiation.

Various multi-photon optical excitation methods have also been employed in a number of laboratory applications in an effort to achieve specific improvements in the selectivity of photo-activation for certain applications, and to address many of the limitations posed by single-photon excitation. Excitation sources ranging from single-mode, continuous wave lasers to pulsed Q-switched lasers having peak powers in excess of 1 GW have been used in these methods. Most efforts have been aimed at using multi-photon excitation as a means for spectroscopically probing excited state properties or for detecting analytes present in strongly absorbing matrices, such as environmental samples. For example, simultaneous two-photon excitation has been used as a means for stimulating fluorescence emission from molecules present in optically dense media (see Wirth and Lytle, Anal. Chem. 49 (1977) 2054–2057; Fisher et al., Appl. Spectrosc. 51 (1997) 218–226). A generalized mechanism for such activation is shown in FIG. 1(b), wherein simultaneous two-photon excitation (12) occurs when a photo-active agent is excited upon absorption of a certain energy $E_1$ that is provided by the simultaneous, combined interaction of two photons $P_1'$ and $P_2'$ with the agent. Note that if the energies of both photons $P_1'$ and $P_2'$ are identical, the excitation process is termed "degenerate". The simultaneous interaction of the two photons is frequently described as being mediated by a transient virtual state V with a lifetime on the order of 10 femtoseconds (fs) or less. If both photons do not interact with the agent during this life time, excitation does not occur and the agent fails to reach $S_n$. Once the agent has been promoted to the higher quantum-mechanically allowed state $S_n$ its photochemical and photophysical properties will be identical to those resulting from single-photon excitation (10). Two-photon excitation has been described for use in microscopy (e.g. Denk et al., U.S. Pat. No. 5,034,613) and as a probe of membrane properties (e.g. Chen and Van Der Meer, Biophys. J. 64 (1993) 1567–1575).

The vast majority of this work appears to have been performed using a single, pulsed excitation source such that the two photons interacting with the molecule are of the same wavelength (the degenerate excitation case). However, non-degenerate (two-color) simultaneous two-photon excitation has also been demonstrated (e.g. Lakowicz et al., Photochem. Photobiol. 64 (1996) 632–635).

Far less commonly, simultaneous three-photon excitation has been described to probe the spectroscopy of molecules such as ammonia (e.g. Nieman and Colson, J. Chem. Phys. 68 (1978) 5656–5657), benzene (e.g. Johnson, J. Chem. Phys. 64 (1976) 4143–4148; Johnson and Korenowsk, Chem. Phys. Lett. 97 (1983) 53–56; Grubb et al., J. Chem. Phys. 81 (1984) 5255–5265; Cable and Albrecht, J. Chem. Phys. 85 (1986) 3155–3164), butadiene (e.g. Johnson, J. Chem. Phys. 64 (1976) 4638–4644), and nitric oxide (e.g. Seaver et al., J. Chem. Phys. 87 (1983) 2226–2231), while simultaneous four-photon spectroscopy has seen even more limited application in studies of molecules such as $NO_2$ (e.g. Rockney et al., J. Chem. Phys. 78 (1983) 7124–7131) and butadiene (e.g. McDiarmid and Auerbach, Chem. Phys. Lett. 76 (1980) 520–524). The general theory of such multi-photon spectroscopies (number of photons$\leq 4$) has previously been described (see Andrews and Ghoul, J. Chem. Phys. 75 (1981) 530–538). Recently, Lakowicz and co-workers have described the use of degenerate, simultaneous three-photon excitation to study the properties of various fluorophors in the condensed phase (see Gryczynski et al., Biophys. J. 71 (1996) 3448–3453; Lakowicz et al., Biophys. J. 72 (1997) 567–578) and as a possible imaging means for microscopy (see Gryczynski et al., Photochem. Photobiol. 62 (1995) 804–808; Szmacinski et al., Biophys. J. 70 (1996) 547–555).

Additional work using multi-photon excitation has sought to elucidate the physical and chemical properties of agents using complex multi-photon excitation methods (see Xing et al., J. Chem. Phys. 194 (1996) 826–831; Wang et al., J. Chem. Phys. 105 (1996) 2992–2997) or to exert quantum control over excited-state reaction pathways using one or more temporally- or spectrally-tailored laser pulses (see Flam, Science 266 (1994) 215–217; Bardeen et al., Chem. Phys. Lett. 280 (1997) 151–158; Service, Science 279 (1998) 1847–1848; Zare, Science 279 (1998) 1875–1879; Clary, Science 279 (1998) 1879–1882). These reported multi-photon methods, however, generally require staged, sequential application of light energy over periods far in excess of 10 fs in order to allow intra-molecular reorganization to occur. FIG. 1(c) shows a generalized representation of such multi-photon activation, wherein 3+2-photon excitation (14) occurs when a photo-active agent is initially excited to a first higher quantum-mechanically allowed state, $S_n$, upon absorption of a certain energy, $E_1$, that is provided by the simultaneous, combined interaction of three photons $P_1''$, $P_2''$ and $P_3''$ with the agent (this interaction is mediated by two virtual states, $V_1''$ and $V_2''$). Subsequent excitation occurs upon absorption of a certain additional energy $E_2$ that is provided by the interaction of the agent with two additional photons $P_4''$ and $P_5''$ to promote it to a second, higher quantum-mechanically allowed state, $S_p$. Typically, there exists a short temporal delay between these two steps $E_1$ and $E_2$, and the second excitation event is often mediated by one or more quantum-mechanically allowed energy states, such as $S_o$.

In contrast, optically-induced quantum control of chemical reactions occurs when an agent is sequentially shuttled between several intermediate states using one or more laser pulses occurring over time frames consistent with electronic bond transformation, relaxation and intra-molecular energy transfer (see Fisher et al., Appl. Spectrosc. 51 (1997) 218–226; Draumer et al., Science 275 (1997) 54–57; Zhong et al., J. Am. Chem. Soc. 119 (1997) 2305–12306), which are now believed to occur on scales between approximately 100 fs and 1 picosecond (ps). FIG. 1(d) shows a generalized representation of such a multi-photon quantum control process (16), wherein excitation occurs via three steps $E_1$ $E_2'$ and $E_3'$ which result from sequential interaction of three photons $P_1'''$, $P_2'''$ and $P_3'''$ with the agent. In this example, the first photon $P_1'''$ serves to excite the agent to state $S_n$, while the second photon $P_2'''$ further excites the agent to state $S_r$. Delivery of photon $P_3'''$ is timed so as to de-excite the agent from $S_r$ to $T_q$, producing a reactive state (and hence leading to a chemical reaction $R_1'$) which is not directly accessible from $S_m$. The temporal delays and multiple quantum-mechanically allowed intermediate states typical of both such multi-photon processes shown in FIGS. 1(c)(14) and 1(d)(16) distinguish them from the simultaneous excitation processes shown in FIG. 1(b)(12), which are essentially single step excitation processes.

Application of quantum control and other specialized excitation methods by Draumer, Zhong, Bardeen and others has lead to the elucidation of two temporal regimes for chemical reactions: (a) a fast regime occurring on the sub-ps time frame, involving intra-molecular electronic transformations; and (b) slow regime occurring on supra-ps time frames, involving intra-molecular reorganization, bond cleavage and inter-molecular interactions. However, events that can be caused to occur in the fast regime can be dramatically different than those possible in the slow regime, since in general the characteristic time constant for fast processes, such as electronic excitation $\tau_{ex}$, is much shorter than that for relaxation $\tau_{relax}$, such as thermal transfer. This implies that if suitably fast excitation processes are used, excitation can be effected, and the resultant effects completed (such as intra-molecular electronic transformations) before significant relaxation processes (such as bond cleavage or thermal transfer) can occur. Such insight has recently begun to see limited application in the fields of photodynamic therapy and laser ablative surgery. Excitation for durations significantly longer than that necessary for interaction in the fast regime (i.e. for ps- to μs-durations) has been found to support photo-activation pathways that are competitive with the desired photo-activation. However, over nanosecond-time-scales, for example, an excited photodynamic agent may absorb additional photons resulting in an undesirable photochemical transformation. This can render agents completely useless for the desired purpose, by transforming a photodynamic therapy agent into a long-lived, systemically-toxic substance (e.g. Shea et al., J. Biol. Chem. 265 (1990) 5977–5982). Furthermore, excitation of events in the slow regime tends to allow energy to leak into surrounding bonds or media which has previously precluded successful quantum control of reactions (due to energy leakage away from desired bonds) and resulted in collateral tissue damage in ablative laser surgery (due to energy leakage into surrounding tissue).

The advent of lasers capable of routinely producing ultrashort pulses (pulse width $\leq 10$ ps), such as the mode-locked titanium:sapphire laser, allows excitation to be substantially limited to the fast regime, vastly improving efficiency of energy delivery to desired treatment targets. The brevity of such pulses substantially precludes competition from alternate photo-activation and relaxation pathways, and should thereby yield controlled activation via only desired mechanisms. For example, Boxer and co-workers (Oh et al., Photochem. Photobiol. 65 (1997) 91–95) and Wachter and co-workers (Fisher et al., Photochem. Photobiol. 66 (1997) 141–155) have recently reported simultaneous two-photon excitation of photodynamic therapy agents, the former demonstrating two-photon spectroscopic properties of psoralen-based agents and the latter demonstrating a two-photon excited photodynamic effect for related agents. In both reports, the use of ultrashort excitation pulses limited photo-activation to the desired mechanism, clearly avoiding competing mechanisms.

Furthermore, Mourou et al. (U.S. Pat. No. 5,656,186) and others attempting to use ultrashort laser pulses to achieve laser-induced breakdown for ablative laser surgery (for example Birngruber et al., IEEE J. Quant. Electron. 23 (1987) 1836–1844; Stern et al., Arch. Ophthal. 107 (1989) 587–592; Watanabe et al., Photochem. Photobiol. 53 (1991) 757–762; Frederikson et al., Arch. Derm. 129 (1993) 989–993; Zair et al., U.S. Pat. No. 5,618,285) have found that the use of pulses with durations less than 10 ps yield substantially finer treatment margins than those achieved using longer pulses as a consequence of the enhanced localization of such effects to the site of optical excitation. Mourou describes laser-induced breakdown as being initiated by multi-photon ionization (18), which is purported to occur as a consequence of non-resonant interaction of NIR light with the aqueous tissue matrix, as shown in FIG. 1(e). Here, the concerted interaction of multiple photons $P_m–P_q$ rapidly promotes water through multiple virtual intermediate states $V_m–V_p$ until ionization occurs (at molecular energies greater than or equal to $S_{ip}$, the ionization potential for water). This process is termed non-resonant because no allowed first-order (single-photon) or multiple-order (two- or more photon) transitions are intentionally accessed (for example, to maximize energy absorption or excitation efficiency).

Surprisingly then, despite the considerable body of theoretical and experimental work with multi-photon spectroscopy and the widespread availability of ultrashort pulsed sources, the inventors are aware of no reports of the general application of ultrashort pulsed, multi-photon methods for therapeutic applications involving selective activation of endogenous (naturally present) or exogenous (externally supplied) molecular agents to produce an enhanced photodynamic or photophysical (ablative) outcome. As explained supra, the work reported to date has been limited solely to two-photon methods or non-specific multi-photon ablation based on non-resonant laser-induced dielectric breakdown.

Thus, while the substantial body of prior work exemplified by works cited herein clearly demonstrates many attractive features of multi-photon photo-activation and the use of ultrashort pulsed sources for effecting such photo-activation, this work has failed to achieve selective photo-activation of one or more molecular agents with a high degree of spatial control and efficiency to meet the diverse needs of the medical field. Specifically, there appears to be no teaching of the use of or practical methods for effecting this control on target agents and materials and on physical scales that are significant for therapeutic applications.

Therefore, it is an object of the present invention to provide flexible and versatile methods for the treatment of plant or animal tissue with a high degree of spacial selectivity.

It is a further object of the present invention to provide such methods using multi-photon optical excitation methods.

It is another object of the present invention to provide such methods using light from a single pulsed light source and endogenous or exogenous photo-active agents to enhance the spatial selectivity and improve the efficiency of such treatment.

It is yet another object of the present invention to provide such methods using wavelengths of light which are in general less harmful to the plant or animal tissue than the wavelengths of light currently used for the treatment of plant or animal tissue.

It is yet another object of the present invention to provide such methods using light which is less prone to scatter in and be absorbed by plant or animal tissue than the wavelengths of light currently used for the treatment of plant or animal tissue.

Consideration of the specification, including the several figures and examples to follow, will enable one skilled in the art to determine additional objects and advantages of the present invention.

SUMMARY OF THE INVENTION

The present invention is directed to a method and apparatus for photo-activating a molecular agent in a particular volume of material using multi-photon excitation.

More specifically, the present invention utilizes the unique physical properties of non-linear optical excitation of one or more endogenous or exogenous therapeutic agents to effect improved spatial control over the photo-activation of such agents via multi-photon photo-activation processes. Such multi-photon photo-activation results from an essentially simultaneous interaction of two or more photons with one or more endogenous or exogenous agents, wherein said photons are provided by a single ultrashort laser pulse having a duration of approximately 10 ps or less. Preferably, for the present invention, the energy and wavelength of the said two or more photons are identical, and as such the excitation processes are termed degenerate.

The multi-photon photo-activations of the present invention allow for a number of therapeutic end points, including those resulting from one or more of the following events: electronic excitation of the one or more agents to a higher quantum-mechanically allowed state; vibrational excitation of the one or more agents to a higher quantum-mechanically allowed state; vibronic excitation (combined vibrational and electronic excitation) of the one or more agents to a higher quantum-mechanically allowed state; and photoionization of the one or more agents. From such excited state end points, the one or more photo-activated agents are made to precipitate desired therapeutic effects, such as photodynamic killing of diseased cells, denaturation of tissue, or ablative removal of tissue.

The multi-photon photo-activation methods taught herein offer specific advantages relative to prior methods, including reduction of collateral excitation and damage along the excitation path, reduction in exposure to harmful optical wavelengths, reduction of interference from absorption and scattering processes originating from the environment surrounding the excited agent, improved treatment depths, improved efficiency of treatment, and enhanced control over location and specificity for the excited agent.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

In describing the preferred embodiments, reference is made to the accompanying drawings:

FIGS. 1(a)–(e) illustrate example energy level diagrams for typical linear and non-linear optical excitation processes;

FIGS. 2(a)–(d) illustrate typical modified Jablonski energy level diagrams for several linear and non-linear optical excitation processes;

FIGS. 3(a)–(b) illustrate an example of modified Jablonski energy level diagrams for hematoporphyrin-IX (Hp-IX) upon simultaneous two-photon excitation and simultaneous five-photon excitation;

FIGS. 7(a)–(b) illustrate examples of spatially localized multi-photon excitation used to locally activate agents present at the surface of tissue or below the surface of tissue;

FIGS. 8(a)–(b) shows a comparison of single-photon and two-photon excited fluorescence of the dye molecule Coumarin-480 distributed evenly throughout a block of agarose gelatin;

FIG. 14 shows another embodiment for treatment of a subsurface lesion using non-focused light.

DETAILED DESCRIPTION OF THE PRESENTLY PREFERRED EMBODIMENTS

Figure 4:
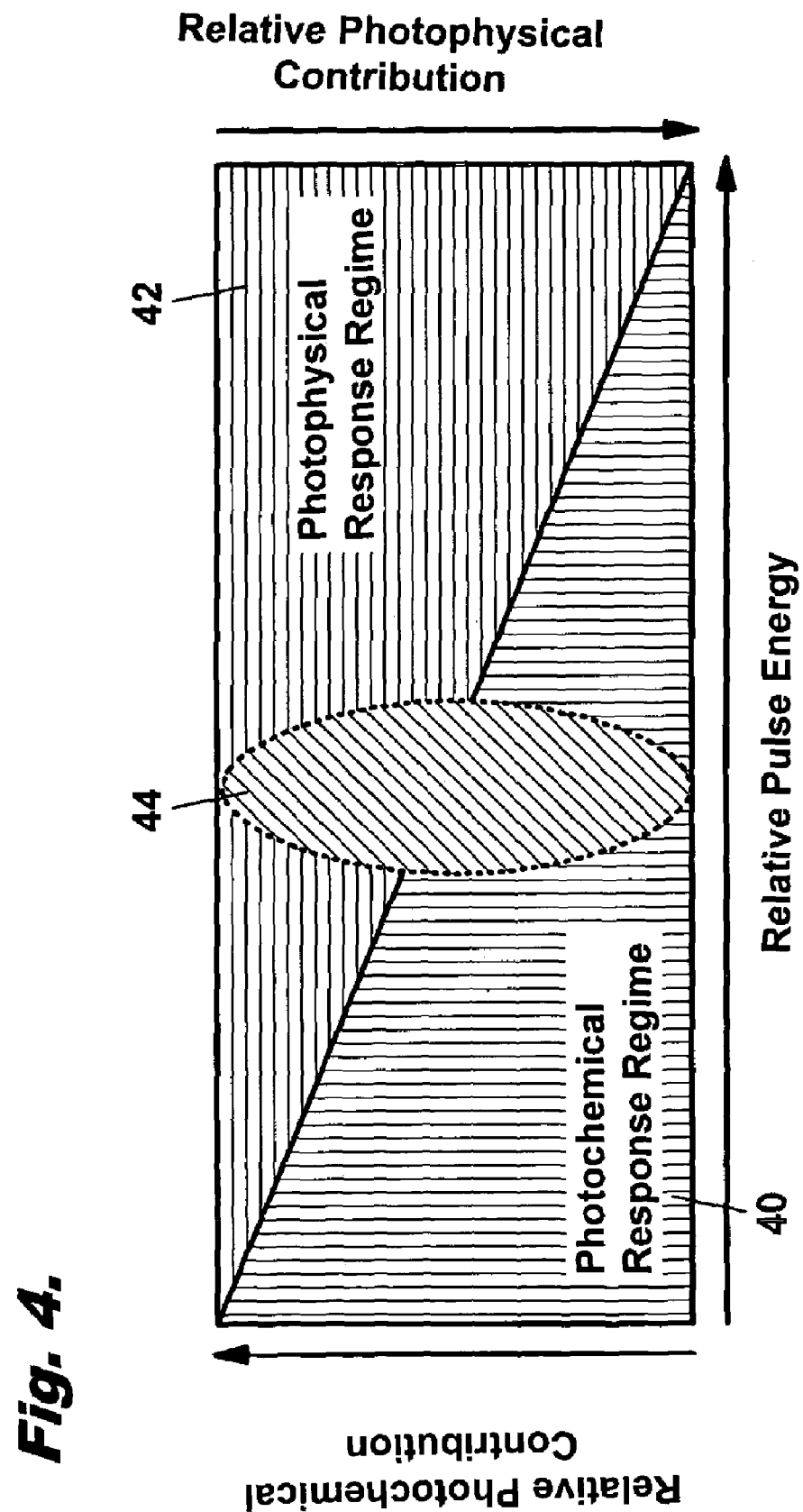
FIG. 4 shows a comparison of relative photochemical and photophysical response of an agent as a function of relative excitation pulse energy.

The present invention described herein utilizes the unique physical properties of non-linear optical excitation of one or more endogenous or exogenous therapeutic agents to effect improved spatial control over the photo-activation of such agents via multi-photon photo-activation processes. "Non-linear optical excitation" is defined for the purposes of this application as those excitation processes involving the essentially simultaneous interaction of two or more photons with the one or more agents. "Essentially simultaneous interaction" is defined for the purposes of this application as those excitation processes occurring as a result of interaction of the one or more agents with photons provided by a single ultrashort laser pulse having a duration of approximately 10 ps or less. "Multi-photon photo-activation" is thus defined for the purposes of this application as non-linear optical excitation occurring as a result of the essentially simultaneous interaction of two or more photons originating from a single ultrashort laser pulse with one or more agents to produce one or more photo-activated agents. Finally, "endogenous agents" are defined for the purposes of this application as photo-active materials pre-existent in a patient or other target, such as for example various proteins; natural chromophoric agents, such as melanin, hemoglobin, and carotenes; water; collagen; and other photo-active materials, such as tattoo dyes. "Exogenous agents" are defined as photo-active materials not pre-existent in a patient or other target, such as for example various photodynamic agents or other photo-active agents administered for the purpose of increasing efficiency of conversion of optical energy into a therapeutic process.

The end point of such multi-photon photo-activation may include one or more of the following events: electronic excitation of the one or more agents to a higher quantum-mechanically allowed state; vibrational excitation of the one or more agents to a higher quantum-mechanically allowed state; vibronic excitation (combined vibrational and electronic excitation) of the one or more agents to a higher quantum-mechanically allowed state; and photoionization of the one or more agents. It is from such excited state end points that the one or more photo-activated agents will thereby precipitate a therapeutic effect, such as photodynamic killing of diseased cells, denaturation of tissue or ablative removal of tissue.

The non-linear optical excitation of the present invention has additional advantages during photo-activation of therapeutic and other agents, including reduction of collateral excitation and damage along the excitation path, reduction in exposure to harmful optical wavelengths, reduction of interference from absorption and scattering processes originating from the environment surrounding the excited agent, and enhanced specificity in the excitation of the agent. The non-linear optical excitation approach employed in the present invention provides a superior means for the treatment of many diseases. The basic configurations of the multi-photon photo-activation method and apparatus for achieving such therapeutic outcomes are described in U.S. patent application Ser. No. 08/739,801, which is assigned to the assignee of the present invention and which has inventors in common with the present application. U.S. patent application Ser. No. 08/739,801 filed Oct. 30, 1996 is incorporated herein by reference in its entirety.

Energy Level Models of Multi-Photon Photo-Activation:

One aspect of the present invention taught in this disclosure lies in the use of multi-photon processes to selectively and efficiently photo-activate one or more therapeutic agent with a high degree of spatial control. This selective photo-activation is achieved by means of harnessing the special properties of non-linear optical excitation to promote an agent from one molecular energy state to another. To fully understand the salient features of this process, a conceptual model of multi-photon photo-activation is developed herein. This is conveniently achieved through use of energy level diagrams for representative cases.

FIGS. 2(a)–(b) illustrate typical modified Jablonski energy level diagrams for several linear and non-linear optical excitation processes.

FIG. 2(a) illustrates single-photon excitation (20) which occurs when an agent is excited from an initial quantum-mechanically allowed state $S_i$ (which is typically the ground state) to a final quantum-mechanically allowed state $S_f$ upon absorption of a certain energy $E_1$ that is provided by interaction of a single photon P with the agent. A number of different allowed final states are possible. Each allowed state may be further subdivided into an ensemble of discrete sub-states, such as various vibrational states superimposed on a particular electronic state. Hence, each allowed state $S_i$ and $S_f$ may constitute a complex band of allowed states that reflect the fundamental properties of the agent and its local environment. In the case of a photodynamic therapy agent, promotion of the agent from $S_i$ to $S_f$ can initiate various therapeutic responses, including for example localized production of cytotoxic species, such as singlet oxygen. As an example, the agent hematoporphyrin-IX (Hp-IX) will generate singlet oxygen upon absorption of energy from a single photon at 400 nm. In single-photon excitation (20), the probability of excitation is linearly related to the irradiance of the incident optical radiation, so single-photon excitation (20) is referred to as a linear excitation process.

In FIG. 2(b), simultaneous two-photon excitation (22) occurs when a photo-active agent is excited from an initial quantum-mechanically allowed state $S_i$ to a final quantum-mechanically allowed state $S_f$ upon absorption of a certain energy $E_1$ that is provided by simultaneous interaction of two photons $P_1$ and $P_2$ with the agent. For all examples consider henceforth, it will be assumed that the energy and wavelength of the two (or more) photons involved in excitation are identical, and as such that the excitation process is termed degenerate. Once the agent has been promoted to the final quantum-mechanically allowed state $S_f$, its photochemical properties will be identical to those resulting from single-photon excitation (20). The simultaneous interaction of the two photons is frequently described as being mediated by a transient virtual state $V_1$ with a lifetime on the order of 10 fs or less. If both photons do not interact with the agent during the life time of this virtual state, excitation does not occur, and the agent returns to allow state $S_i$. Due to the exceedingly short lifetime of the virtual state $V_1$ the instantaneous irradiance, or W m$^{-2}$ of the incident excitation light must be sufficiently high to yield significant efficiency in absorption of the second photon $P_2$ before the virtual energy state $V_1$ undergoes relaxation back to $S_i$. Hence, pulsed excitation sources having very high peak powers are commonly used to efficiently stimulate this process; such sources are often preferable since they are capable of providing large numbers of photons to the excited agent during the brief lifetime of the virtual state $V_1$.

An example of simultaneous two-photon excitation (22) is the promotion of singlet oxygen generation from Hp-IX through the simultaneous absorption of two photons at 800 nm. In this example, the probability of excitation is related to the product of the instantaneous irradiance of the first of photon $P_1$, and the second photon $P_2'$ This can be conceptualized in the form of a photochemical reaction, $$\text{Agent}_{GROUND\ STATE} + 2h\nu_{800\ nm} \rightarrow \text{Agent}_{EXCITED\ STATE} \quad (1)$$

which shows that an agent in the ground state is promoted to an excited state following simultaneous absorption of two photons, $h\nu_{800\ nm}$, each at 800 nm. The reaction rate R is given by R=k $[\text{Agent}_{GROUND\ STATE}]$ $[h\nu_{800\ nm}]^2$, where k is an intrinsic reaction rate constant for the agent and where $[\text{Agent}_{GROUND\ STATE}]$ $[h\nu_{800\ nm}]$ symbolize concentrations of agent molecules in the ground state and the excitation photons, respectively. Hence, due to the quadratic dependence on instantaneous irradiance, simultaneous two-photon excitation (22) is referred to as a non-linear excitation process.

In FIG. 2(c), simultaneous three-photon excitation (24) occurs when a photo-active agent is excited from an initial quantum-mechanically allowed state $S_i$ to a final quantum-mechanically allowed state $S_f$ upon absorption of a certain energy $E_1$ that is provided by simultaneous interaction of three photons $P_1'$, $P_2'$ and $P_3'$ with the agent. The simultaneous interaction of the three photons is described as being mediated by two transient virtual states $V_1'$ and $V_2'$ each having a lifetime on the order of 10 fs or less. If all three photons do not interact with the agent during these life times, excitation does not occur and the agent returns to $S_i$. Due to the exceedingly short lifetime of the virtual states $V_1'$ and $V_2'$ the instantaneous irradiance of the incident excitation light must be sufficiently high to yield significant efficiency in absorption of the second photon $P_2'$ and the third photon $P_3'$ before the agent undergoes relaxation back to $S_i$. An example of simultaneous three-photon excitation (24) is the promotion of singlet oxygen generation from Hp-IX through the simultaneous absorption of three photons at 1200 nm. In this example, the probability of excitation is related to the product of the instantaneous irradiance of the first photon $P_1'$, the second photon $P_2'$ and the third photon $P_3'$. This can be conceptualized in the form of a photochemical reaction, $$\text{Agent}_{GROUND\ STATE} + 3h\nu_{1200\ nm} \rightarrow \text{Agent}_{EXCITED\ STATE} \quad (2)$$

which shows that an agent in the ground state is promoted to an excited state following simultaneous absorption of three photons, $h\nu_{1200\ nm}$, each at 1200 nm. The reaction rate R is given by R=k $[\text{Agent}_{GROUND\ STATE}]$ $[h\nu_{1200\ nm}]^3$, where $[h\nu_{1200\ nm}]$ symbolizes the concentration of excitation photons. Hence, due to the cubic dependence on instantaneous irradiance, simultaneous three-photon excitation (24) is also referred to as a non-linear excitation process.

In FIG. 2(d), simultaneous multi-photon excitation (26) occurs when a photo-active agent is excited from an initial quantum-mechanically allowed state $S_i$ to a final quantum-mechanically allowed state $S_f$ upon absorption of a certain energy $E_1$ that is provided by simultaneous interaction of two or more photons with the agent. Once the agent has been promoted to the final quantum-mechanically allowed state $S_f$, its photochemical properties will be identical to those resulting from single-photon excitation (20). The simultaneous interaction of the two or more photons is often described as being mediated by a corresponding multiplicity of one or more virtual states, each having a lifetime on the order of 10 fs or less. If all photons do not interact with the agent during these lifetimes, excitation does not occur and the agent returns to $S_i$. Due to the exceedingly short lifetime of the one or more virtual states, the instantaneous irradiance of the incident excitation light must be sufficiently high to yield significant efficiency in absorption of all photons before the agent undergoes relaxation back to $S_i$. An example of simultaneous multi-photon photo-activation (26) is the promotion of singlet oxygen generation from Hp-IX through the simultaneous absorption of n photons at a wavelength ($\lambda$) of (400*n) nm (for example, if n=2, $\lambda$=800 nm; if n=3, $\lambda$=1200 nm; and so on for n$\geq$2). In this example, the probability of excitation is related to the product of the instantaneous irradiance of the n photons. This can be conceptualized in the form of a general photochemical reaction, $$\text{Agent}_{GROUND\ STATE} + nh\nu \rightarrow \text{Agent}_{EXCITED\ STATE} \quad (3)$$

which shows that an agent in the ground state is promoted to an excited state following simultaneous absorption of n photons. The reaction rate R is given by R= k $[\text{Agent}_{GROUND\ STATE}]$ $[h\nu]^n$, where $[h\nu]$ symbolizes the concentration of the n excitation photons. Hence, due to the non-linear dependence on instantaneous irradiance, simultaneous multi-photon photo-activation (26) is also referred to as a non-linear excitation process.

A more general definition of multi-photon excitation than that given above requires only that the two or more photons interact with the one or more agents in a substantially simultaneous manner, for example any interaction occurring during a single ultrashort laser pulse having a duration of approximately 10 ps or less. Under such constraints, the interaction of light with the one or more agents must occur in the fast regime, substantially limiting (and localizing) the direct photo-activation effect to intra-molecular processes, such as electronic excitation or photoionization of the agent. No significant elapse of time nor substantial molecular reorganization nor motion will occur during such excitation, and on conventionally observable frames of reference any transitions thereby effected in the one or more agents will occur as an essentially single, concerted step. This more general definition shall be used in subsequent descriptions of the properties of multi-photon excitation and of the resultant multi-photon photo-activation of therapeutic agents.

In addition to the specific examples of photochemical processes and energy diagrams shown in reference to FIG. 2, many other possible transitions and energy level conditions are possible, depending upon numerous factors, including the characteristics of the molecular system, its environment, and the particular energies of the absorbed and released forms of energy, along with their temporal and spatial correlations.

Role of Photon Energy and Instantaneous Irradiance in Multi-Photon Photo-Activation:

For the foregoing examples, once the agent has been promoted to the final quantum-mechanically allowed state $S_f$ following absorption of a particular quantity of energy $E_1$ its photochemical properties will be identical regardless of the means used for such promotion. These properties will be determined by the intrinsic properties of the excited agent and its local environment. The particular final energy state $S_f$ attained will be determined by the magnitude of the total energy $E_1$ delivered to the molecule. Hence, it is the magnitude of $E_1$ that will ultimately determine the photochemical or photophysical properties of the agent upon arrival at $S_f$.

For example, FIG. 3(a) shows an agent, such as e.g. Hp-IX, undergoing simultaneous two-photon excitation (30) with a total absorbed optical energy ($E_1$) equivalent to 3.1 eV ($E_1$ is calculated according to the relationship $E_1=2hv$, where $E_1$ represents the combined energy of 2 photons $P_n$ each of which has a wavelength of 800 nm and an energy of 1.55 eV). The agent will be stimulated to undergo photodynamic production of singlet oxygen from its excited state according to the reaction $R+2hv \rightarrow R^*$ (where R is the un-excited, or ground state, agent, and $R^*$ is the reactive excited agent).

FIG. 3(b) illustrates the same agent undergoing simultaneous five-photon excitation (32) with a total absorbed optical energy ($E_1'$) equivalent to 7.8 eV. $E_1'$ is calculated according to the relationship $E_1'=5hv$, where $E_1'$ represents the combined energy of 5 photons $P_n'$ each of which also has a wavelength of 800 nm. The agent will be photoionized according to the reaction $R+5hv \rightarrow R^+ + e^-$ (where $R^+$ is the ionized form of the agent, and $e^-$ is an electron removed from the agent during photoionization).

Hence, FIGS. 3(a)–(b), illustrate how, through proper selection of specific photon energy and instantaneous irradiance, the photochemical and photophysical outcomes of an excitation process for a given agent can be controlled to achieve a desired outcome (such as a photodynamic process or photoionization).

More generally, by varying the instantaneous irradiance delivered to the agent (at a given specific photon energy), the energy of the excited state can be varied according to the relationship, $E=n\,hv$, where n is the number of photons absorbed. As this energy is increased, for example by increasing the pulse energy of a laser excitation source, the therapeutic outcome of the interaction of light with an agent can be shifted from a substantially photochemical process to a substantially photophysical process, as shown diagrammatically in FIG. 4. At low relative pulse energies, for example less than 10 nJ delivered in a 200 fs pulse, photochemical excitation (40) via two- or three-photon processes will typically predominate. However, at high relative pulse energies, for example greater than 100 µJ delivered in a 200 fs pulse, photophysical excitation (42) via a four- or more photon process will typically predominate. At intermediate relative pulse energies a combination outcome (44) is possible (part photochemical, part photophysical in nature, such as thermal denaturation or highly localized coagulation). Thus, use of the present multi-photon methods allows therapeutic processes to be shifted between regimes ranging from photodynamic to ablative.

Non-Linear Relationships in Multi-Photon Photo-Activation:

Once an agent has been promoted to an excited state, a variety of physical or chemical processes may occur, including luminescent emission of a photon, photochemical transformation, such as isomerization, oxidation or polymerization, or photoionization. It is the fundamental properties of the excited state and its environment that determine the ultimate fate of the agent. When ultrashort pulsed excitation methods are used, the mechanism responsible for promoting the agent to the excited state has no significant impact on this fate since the excitation process itself does not directly impact the subsequent properties of the excited agent or its environment.

Figure 5:
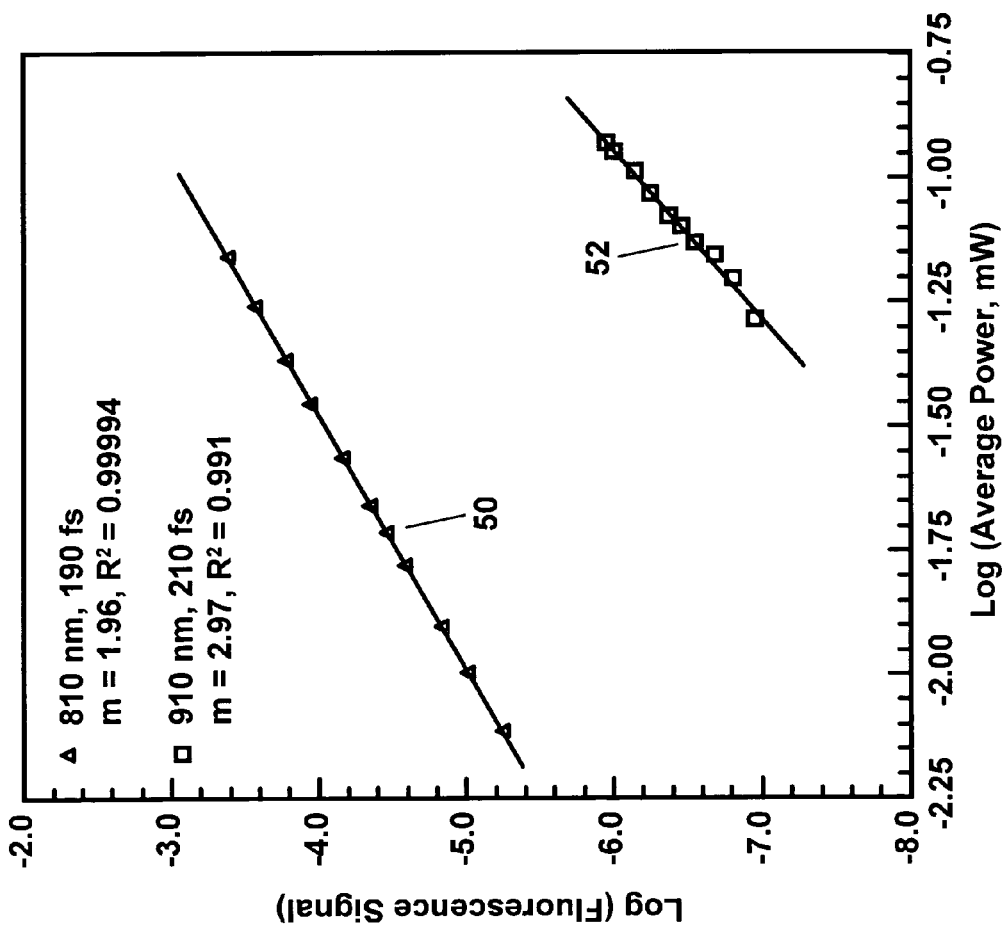
FIG. 5 shows a comparison of two-photon excitation response and three-photon excitation response for Indo-1 as a function of excitation power.

Accordingly, the feasibility of multi-photon excitation for a given agent can be readily evaluated through examination of one or more of these responses as a function of excitation power (which correlates directly with instantaneous irradiance). By measuring agent response at several excitation powers, successful multi-photon excitation can be confirmed by plotting $\log_{10}$(response) against $\log_{10}$(power). This should produce a straight line with a slope of n, where n is the number of excitation photons absorbed by the agent under the particular test conditions. This is readily demonstrated for the fluorescent probe agent Indo-1, which exhibits strong single-photon excitation (emitting fluorescence at 500 nm) upon illumination with light between 300 and 400 nm. When this agent is illuminated using focused light at 810 nm and $\log_{10}$ (fluorescence signal) is plotted against $\log_{10}$(average power), as shown in FIG. 5, two-photon excitation response (50) is noted (slope m=1.96, correlation coefficient $R^2=0.99994$). The focused light is, for example, a beam composed of a 76 MHz repetition rate train of approximately 200 fs pulses produced by a mode-locked titanium:sapphire laser. When a similar test is performed at 910 nm, Indo-1 exhibits a three-photon excitation response (52) as a function of laser power (m=2.97, $R^2=0.991$). In comparison, the fluorescent agent Coumarin-540A, which exhibits only a two-photon response at these wavelengths, exhibits slopes of 2.01 and 2.00 at 810 nm and 910 nm, respectively. At these wavelengths, the multi-photon signals completely disappear if the laser is not pulsed, confirming that multi-photon excitation is responsible for the observed response (since the non-pulsed laser beam does not provide sufficient instantaneous irradiance to support a multi-photon process with these agents at these wavelengths).

Additionally, the excitation cross-sections for multi-photon processes generally decrease as the number of photons required for a given transition increases. For example, the three-photon cross-section for a particular transition in a given agent will generally be lower than the respective two-photon cross-section for the same transition. This is at least in part due to the reduced probability that all photons necessary for a particular multi-photon process will interact with the agent in a substantially simultaneous manner. This is evident when comparing the magnitude of the two-photon excitation response (50) and the three-photon excitation response (52) for Indo-1 (FIG. 5) at a given average excitation power. However, since the slope of the three-photon process is steeper than that of the two-photon process, this difference in relative cross-section can be substantially ameliorated by increasing the instantaneous irradiance of the excitation light, for example by decreasing pulse width for a beam of a given average power, or by increasing pulse energy (for example by using an amplified light source, such as a regeneratively amplified titanium:sapphire laser or a chirp-pulse amplified Nd:YAG laser). The latter approach may lead to changes in the relative ratio of photophysical and photochemical processes, however, as illustrated in FIG. 4, and may thus be undesirable under certain circumstances. In fact, this is the origin of the occurrence of photoionization and ablation at extremely high pulse energies, which require a relatively large number of photons and hence are observed to a significant extent only when the instantaneous irradiance is exceptionally high, for example when pulse energy is exceptionally high. Likewise, the former approach to increasing multi-photon excitation yield may fail if pulse width is decreased excessively, since the resultant optical bandwidth of the excitation pulse can become so large that the intensity at wavelengths responsive to the agent becomes substantially reduced. For example, if the pulse width is reduced below 10 fs, the optical bandwidth may exceed 100 nm, spreading energy of the beam over too wide a range of wavelengths to effectively stimulate a particular transition.

Figure 6:
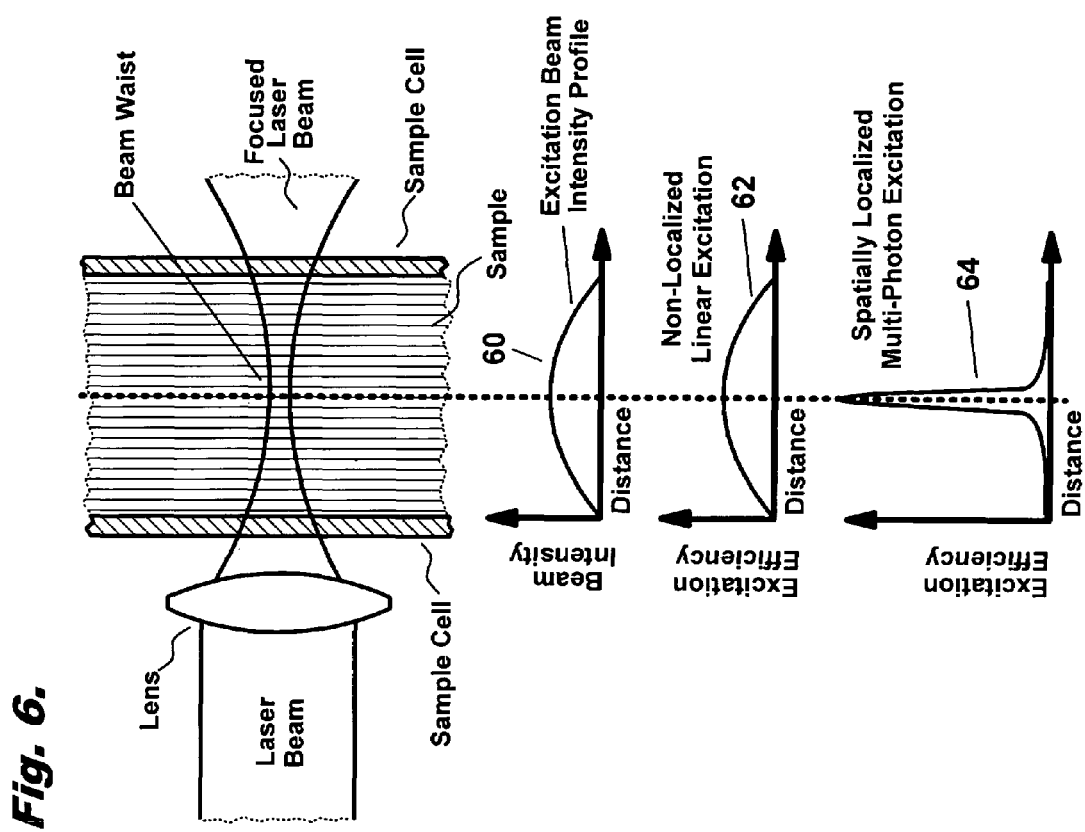
FIG. 6 shows a comparison of spatial excitation properties for linear and non-linear excitation processes.

Spatial Properties of Multi-Photon Photo-Activation:

Because multi-photon photo-activation is non-linear with instantaneous irradiance, such processes exhibit an important and dramatic difference in spatial excitation properties relative to linear excitation processes. For example, as shown in FIG. 6, if a laser beam is focused into a material a beam intensity profile (60) will be produced that varies as a function of distance through the sample, reaching a maximum level at the center of the focus as predicted by classical Gaussian optical theory. For a single-photon process, the linear relationship between beam intensity (or instantaneous irradiance) and excitation efficiency results in a single-photon excitation efficiency profile (62) that follows the beam intensity profile (60). In contrast, for multi-photon processes, the non-linear relationship between beam intensity (or instantaneous irradiance) and excitation efficiency (such as proportionality to $I^2$ or $I^3$ for two- or three-photon processes, respectively, where I is instantaneous irradiance at any position in the sample) results in an excitation efficiency profile (64) that is significantly sharper than the beam intensity profile (60). This spatial localization of excitation can thus be used to substantially limit the extent of excitation to a small focal zone when multi-photon excitation is employed. In contrast, when linear excitation is employed, excitation occurs substantially along the entire optical path, making spatial localization of excitation considerably less defined. Such spatial localization may be observed in both transparent media, such as the eye, and in optically dense media, such as dermal tissue. Thus, spatially localized multi-photon excitation may be used to locally activate agents present at the surface of tissue (70) or below the surface of tissue (72), as shown for example in FIGS. 7(a) and 7(b), respectively.

Figure 8A:
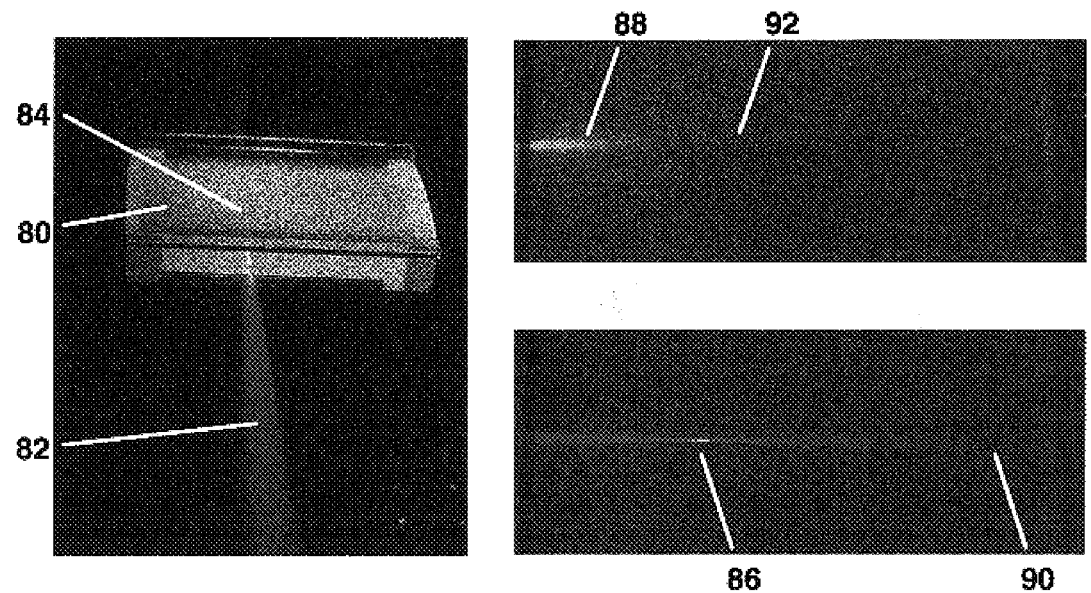

Stimulation of a localized, remote photo-activated response in an optically dense medium is demonstrated in FIGS. 8(a) and 8(b). FIG. 8(a) shows a photograph of a solid block of agarose gelatin (80) throughout which the dye molecule Coumarin-480 has been evenly distributed. FIG. 8(b) is a drawing of the photograph in FIG. 8(a). The agarose gelatin (80) constitutes an optically dense medium since it strongly scatters visible light. Coumarin-480 emits blue fluorescent light when excited via single-photon methods at 350–450 nm or when excited via two-photon methods at 700–900 nm.

In this example, a beam of light (82) was focused into the agarose gelatin (80) from one side such that it formed a focus (84) approximately 2 cm into the gelatin. Specifically, either a beam (82) of visible light (at 400 nm) or of NIR light (at 730 nm from a mode-locked titanium:sapphire laser) was expanded to produce a collimated beam approximately 50 mm in diameter using a beam expanding telescope. The laser produced continuous train of <200 fs pulses of 730 nm light at a 76 MHz pulse repetition frequency. The expanded beam was then focused into the agarose gelatin (80) using a 250 mm focal length (f.l.), 50 mm diameter biconvex singlet glass lens. The agarose gelatin (80) was then positioned such that the focus (84) of this 250-mm f.l. lens fell at a position 2 cm into the agorose gelatin (80). Now, from a perspective looking directly down onto the agarose gelatin (80) from above the optical axis defined by the beam of light (82), FIGS. 8(a) and 8(b) clearly show that fluorescence from the Coumarin-480 is only stimulated at the focus of the NIR beam (86), while fluorescence is emitted along the entire line of flight for the visible beam (88). Moreover, a large fraction of the NIR beam (90) continued through the entire thickness of the agarose gelatin (80) with only slight attenuation, while the visible beam (92) was completely extinguished before traversing one third of the thickness of the agarose gelatin (80).

The features observed in FIGS. 8(a) and 8(b) dramatically illustrate the unique spatial localization achievable with multi-photon excitation, along with the generally improved penetration of NIR light relative to shorter wavelength light in optically dense media (such as an agarose gelatin (80) or human or animal tissue). Because of the non-linear relationship between efficiency of multi-photon excitation and instantaneous irradiance, agent stimulation at positions along the beam path prior to and after the focus is negligible. Hence, little or no collateral photo-activation occurs outside the focal zone. Also, because the NIR excitation light is only weakly absorbed or scattered by the gelatin, sharp focus is maintained at deep penetration depths into the block (in fact, by moving the gelatin along the optical axis, sharp focus was achievable through the entire 8-cm thickness of gelatin). Since the sharpness of the focus observed in FIGS. 8(a) and 8(b) is determined by Gaussian optical properties, the length of the focal zone is easily adjusted by changing the optical parameters used for beam manipulation.

As the number of photons employed for excitation is increased, the multi-photon excitation efficiency profile (64) shown in FIG. 6 and evidenced in FIGS. 8(a) and 8(b) will become increasingly tighter. Hence, three-photon excitation will provide tighter spatial localization than that possible with two-photon excitation, and so on. This implies that the multi-photon order (number of photons utilized for a particular excitation) can be optimized to match the spatial properties of the resultant focal zone to that of the target. For example, the thickness of the focal zone might be tightened through the use of three-photon excitation in order to optimize selective activation of agent at the surface of tissue (70), as shown in FIG. 7(*a*).

In addition to this quantum-mechanically based spatial localization of photo-activation, use of ultrashort pulsed excitation to achieve multi-photon photo-activation prevents substantial energy leakage from the target site during the excitation process, further localizing the effects of such excitation. For example, in the case of simultaneous two-photon or three-photon excitation, molecular reorganization or translation is not possible during ultrashort pulsed excitation events, and thus all absorbed excitation energy is made available to activate the desired transitions in the one or more photo-active agents. Similarly, in the case of ablative processes resulting from multi-photon excitation, thermal leakage of excitation energy away from the target site cannot occur on time frames comparable to ultrashort excitation pulses. Therefore, all energy present during such pulses remains available to activate the desired transitions, such as for example the photoionization processes that serve to trigger ablation. This contributes to extremely rapid, highly localized, and efficient photoionization of agents present in the target zone and results in expeditious ablation of said activated agents before energy leakage can occur to the surrounding media—thus further contributing to spatial localization of the photo-activation process.

Spectral Response Properties of Multi-Photon Photo-Activation:

In addition to dramatic differences in spatial excitation properties, the selection rules governing efficiency of excitation as a function of wavelength may be vastly different for single-photon and multi-photon excitation. However, the properties of the specific excited state accessed will be the same regardless of the excitation mechanism used to promote the agent to that particular excited state.

Figure 9:
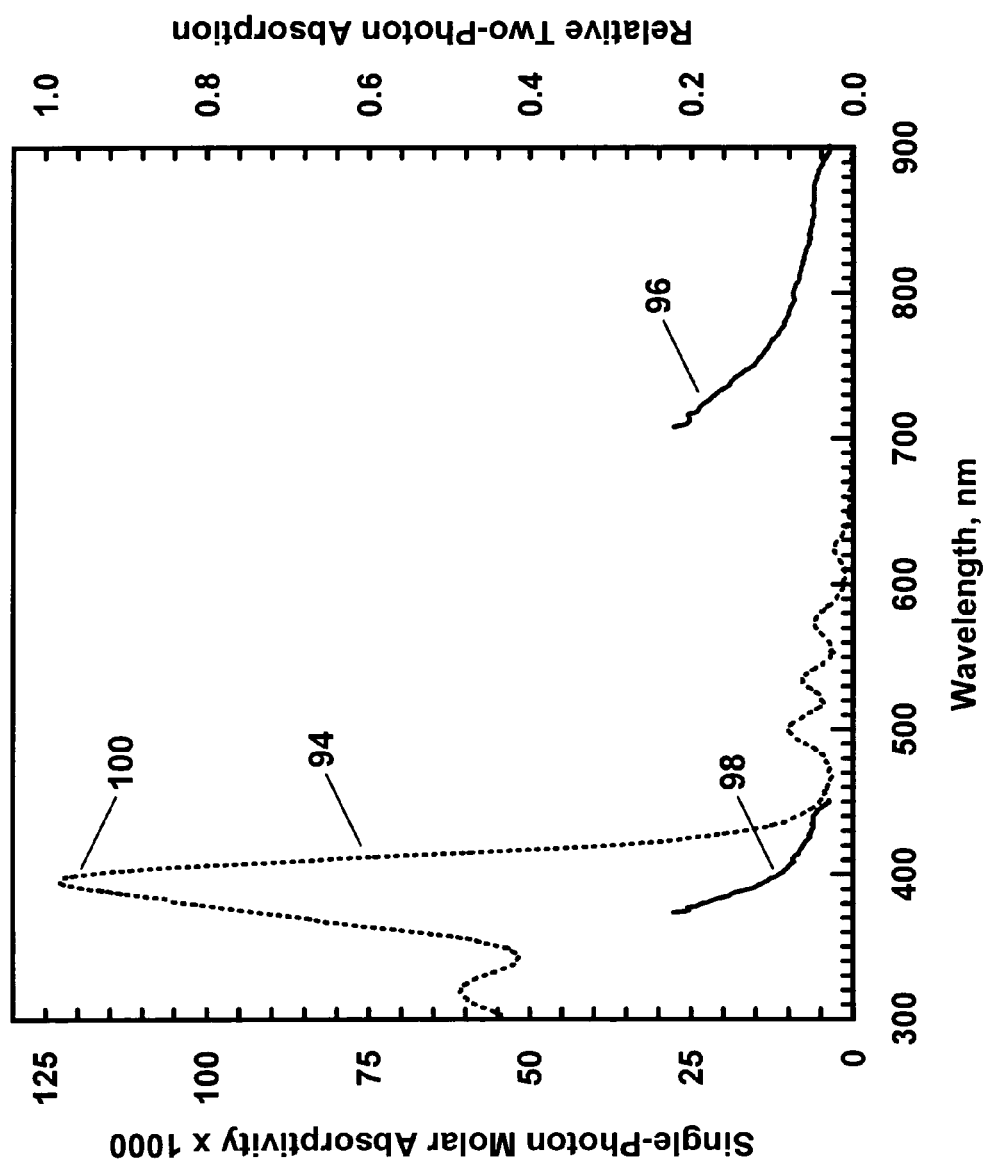
FIG. 9 compares absorption cross-sections as a function of excitation wavelength for Hp-IX when using single-photon excitation and simultaneous two-photon excitation.

FIG. 9 provides an example showing a relative comparison of absorption cross-sections as a function of excitation wavelength for Hp-IX in ethanol when using conventional single-photon excitation (94) and simultaneous two-photon excitation (96). Additionally, the simultaneous two-photon excitation (96) data is also plotted using a wavelength scale that has been divided by two (98) to reflect that simultaneous two-photon excitation is equivalent in energy to absorption of a single photon at twice the energy (or one half the wavelength) of the each of two photons. Comparison of the relative cross-sections for single-photon excitation (94) and for simultaneous two-photon excitation plotted at the one-half wavelength scale (98) shows significant differences as a function of wavelength. Specifically, the prominent Sorrett band (100) evident with single-photon excitation (94) is absent for simultaneous two-photon excitation (96) or (98), since it is quantum-mechanically dis-allowed.

Such differences are attributable to differences in selection rules for particular molecular transitions that are dependent on the mechanism employed in excitation, and are useful for optimizing efficiency or selectivity of excitation based on the differences in multi-photon selection rules, and in designing specific agents with special multi-photon properties. In general, for centrosymmetric agents (those containing a center of inversion), an excitation process employing an even number of photons (such as for example two-photon excitation) must raise an agent from its initial state to an excited electronic state having like parity. This is the exact opposite of the selection rules for an excitation process employing an odd number of photons (such as single-photon excitation), and accounts for the differences in the Sorrett band (100) response for Hp-IX observed in FIG. 9. In contrast, agents with little or no symmetry will in general have identical selection rules regardless of the number of photons employed in their excitation. Thus, for centrosymmetric agents, it will generally be advantageous to carefully determine multi-photon spectral response as a function of wavelength in order to determine optimal excitation wavelengths, while for non-centrosymmetric agents, single-photon excitation spectra may generally be used to estimate multi-photon spectral response as a function of wavelength.

Figure 10:
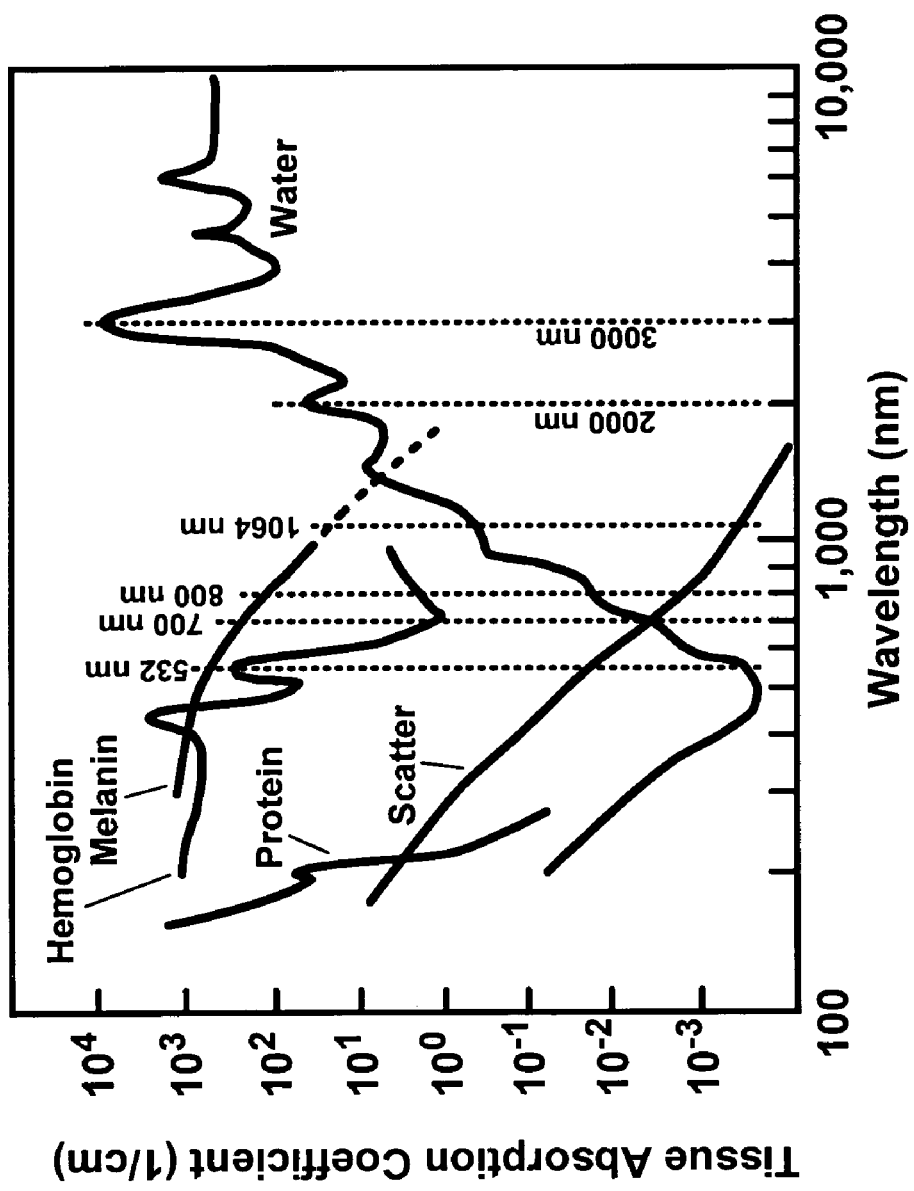
FIG. 10 shows example absorption and scatter spectra for human tissue covering the ultraviolet to infrared spectral region.

Significance of Tissue Absorbance and Scattering Properties in Multi-Photon Photo-Activation:

While the cross-section for multi-photon excitation may be considerably lower than that observed with single-photon excitation, use of the multi-photon methods may be favorable to conventional excitation methods under many conditions because of lower matrix absorption and optical scattering of longer wavelength optical radiation. For example, FIG. 10 shows typical absorption and scattering properties for tissue covering the UV to IR spectral region. Several conclusions are clear from FIG. 10.

First, use of longer wavelength light reduces the relative effects of scatter, and thereby improves optical penetration depth. Hence, substitution of a multi-photon method for a conventional, single-photon method will reduce the effects of scatter on the delivery of activating light to an agent present within tissue. For example, use of two-photon excitation at 700 nm or three-photon excitation at 1050 nm to activate a UV-active PDT agent, such as psoralen, that is normally activated using 350 nm light, will result in an approximate 100-fold to 2000-fold reduction in scatter for 700 nm and 1050 nm light, respectively.

Second, interferences from tissue absorbance, which can reduce penetration of activating light and result in collateral tissue damage outside of the desired treatment site, is generally reduced through the use of longer wavelength light, for example, NIR light in the so-called tissue transmission window extending from approximately 700 nm to 1300 nm. Hence, substitution of a multi-photon method for a conventional, single-photon method will usually reduce the effects of tissue absorbance on the delivery of activating light to an agent present within tissue. For example, use of two-photon excitation at 700 nm or three-photon excitation at 1050 nm to activate a UV-active PDT agent, such as psoralen, that is normally activated using 350 nm light, will result in an approximate 70-fold to 2000-fold reduction in absorbance for 700 nm and 1050 nm light, respectively, in melanotic tissue, and an approximate 260-fold to 3500-fold reduction in absorbance for 700 nm and 1050 nm light, respectively, in non-melanotic tissue. Hence, the use of agents that are characterized by single-photon excitation wavelengths that overlap with spectral regions of high tissue absorbance becomes feasible for deep-tissue applications through the use of multi-photon methods, since such methods enable delivery of activating light to deep tissue locations without interference from tissue absorption.

Reduced scatter and absorption by tissue allows spatially-localized excitation to be efficiently realized with multi-photon methods, as illustrated in FIGS. 7 and 8, since matrix interference is substantially reduced. Furthermore, reduced scatter and absorption by tissue results in additional safety advantages for multi-photon photo-activation. For example, when UV light impinges on human tissue the majority of the optical energy is immediately absorbed and scattered in the outermost layers, such as the epidermis and dermis. Absorption may occur due to excitation of certain molecules in the cells of this tissue, such as those composing the genetic material in the cellular nucleus. This absorption of high-energy light by cellular constituents can thereby initiate a variety of collateral photochemical changes in these cells, including irreversible genetic damage and induction of cancer. In contrast, NIR light used for two-photon or three-photon methods will not be appreciably absorbed or scattered by tissue, and as such the possibility for collateral damage to cells will be substantially lower.

Selection of Excitation Wavelengths for Multi-Photon Photo-Activation:

The foregoing discussion on the role tissue properties play in the overall efficiency of multi-photon photo-activation suggests an equally important point: the order of a multi-photon process (i.e. the number of photons utilized for excitation) can be chosen to simultaneously optimize the excitation wavelength of the one or more desired photo-active agents and the transmissive properties of tissue. Specifically, to activate one or more exogenous photo-active agents, it will in general be desirable to choose a particular multi-photon process that permits excitation using light in a transmissive region for the matrix (such as tissue) and that is efficient in photo-activation of the desired exogenous agent or agents. Similarly, to activate one or more endogenous photo-active agents, it will in general be desirable to choose a particular multi-photon process that allows excitation using light in a transmissive region for the matrix (such as tissue) and that is efficient in photo-activation of the desired endogenous agent or agents. In the case where the one or more endogenous agents constitutes a major component of the tissue to be treated, proper selection of the multi-photon process will generally allow spatially-localized photo-activation of such agents even at subsurface locations (since interference from direct, linear absorption of the activating light can be minimized). This is clearly illustrated in FIGS. 8(a) and 8(b), where selective, efficient activation of an agent (86) is demonstrated deep within a specimen through which the agent is uniformly distributed. In contrast, conventional activation methods yield agent activation (88) that is not spatially localized and that exhibits poor efficiency at such depths due to absorbance of the activating light by the agent along the optical path.

Hence, an example of the selection of multi-photon process order for simultaneous optimization of photo-activation efficiency and tissue transmissive properties is the activation of psoralen in a non-melanotic tissue. In this example, the large two-photon cross-section of psoralen relative to the corresponding three-photon cross-section would allow efficient photo-activation of psoralen using two-photon excitation at 700 nm with an approximate 260-fold reduction in tissue absorbance relative to single-photon excitation at 350 nm. As an alternate example, activation of psoralen in melanotic tissue affords further illustration. In this example, the large absorbance of light at 700 nm by melanin indicates that use of longer wavelengths would be preferable to avoid matrix interferences and as such three-photon activation of psoralen at 1050 nm would be optimal as a consequence of the approximate 15-fold reduction in tissue absorbance of light at 1050 nm relative to 700 nm and the approximate 3500-fold reduction in tissue absorbance of light at 1050 nm relative to 350 nm.

It should be noted that in general the most desirable wavelengths for multi-photon excitation will fall between 500 nm and 4000 nm as a consequence of the favorable tissue transmission properties in this band. Moreover, the order of a particular multi-photon process will be chosen to allow operation in the desired photochemical/photophysical regime, such as that illustrated in FIG. 4. For example, if a photochemical process, such as PDT, is a desired therapeutic outcome, a high-order process requiring an excessively high pulse energy will be less desirable due to potential for interference from photophysical processes.

Excitation Sources for Multi-Photon Photo-Activation:

The cross-section for a particular multi-photon excitation process is typically many-fold smaller than that for an equivalent single-photon excitation process yielding the same activated state as the multi-photon process. This is due to the relatively low probability that two or more photons will interact with an agent in a substantially simultaneous manner. However, the availability of optical excitation sources capable of providing high instantaneous irradiance, such as mode-locked lasers (including titanium:sapphire lasers and Nd:YAG lasers) and amplified mode-locked lasers (including the regeneratively amplified titanium:sapphire laser and chirp-pulse amplified Nd:YAG lasers), can substantially ameliorate the impact of this low efficiency by increasing incident instantaneous irradiance and thereby dramatically increasing the effective efficiency of multi-photon excitation. Such lasers typically offer ultrashort pulsed output (having pulse widths ranging from 10 fs to 10 ps) at high pulse repetition rates (ranging from 1 kHz to 100 MHz) with modest average powers (ranging from 1 mW to 10 W). Such output properties facilitate selective, efficient multi-photon photo-activation, since the high instantaneous irradiance obtainable is capable of stimulating multi-photon processes while the short pulse widths and modest average powers minimize undesirable energy leakage to surrounding media. For example, when using continuous wave excitation, the efficiency of three-photon excitation for a particular agent may be a factor of $10^7$ or more smaller than that achievable with single-photon excitation. However, if the same average optical power is emitted in the form of a train of ultrashort pulses, the shift in production of the instantaneous and average irradiance can change this ratio such that it is close to unity. The special properties of ultrashort pulsed excitation allows this dramatic improvement without concomitant increases in collateral damage.

Note that sources capable of emitting relatively low energy pulses (such as the mode-locked titanium:sapphire laser, with typical pulse energies in the range of 1–10 nJ) are optimally suited to photochemical activation of agents (such as PDT) using two- or more photons under focused illumination conditions, while sources capable of emitting relatively high energy pulses (such as the regeneratively amplified titanium:sapphire laser, with typical pulse energies in the range of 1–10 µJ) are optimally suited to photophysical activation of agents (such as ablation) using two- or more photons under focused illumination conditions. These same high pulse energy sources are also optimally suited to photochemical activation of agents (such as PDT) using two- or more photons under non-focused illumination conditions, for example to activate agents over a large area or within a large volume of tissue.

Therapeutic Applications of Simultaneous Two-Photon Excitation:

The foregoing discussions suggests that the fundament differences between the absorption of UV and visible light and of NIR and IR light by tissue and cellular constituents, coupled with the special non-linear properties of multi-photon excitation, should have direct applicability for improvements in the treatment of disease, specifically in the fields of PDT, selective tissue denaturation, and laser surgery.

PDT utilizes optical energy to photo-activate agents that have been administered to diseased tissue. The route for administration of these agents is typically topical application directly to a diseased tissue or via systemic administration. Under ideal conditions, the PDT agents will partition into or otherwise become concentrated on or in the diseased tissue. Following administration of the PDT agent, optical radiation is used to excite photochemical changes in the PDT agent that lead to a therapeutic effect. These photochemical changes will in general lead to localized cessation of cell proliferation or to cell necrosis in the lesion. The multi-photon photo-activation methods taught in the present invention, when used to activate PDT agents, allow improved penetration of the activation light to deeply seated treatment zones, improved treatment localization, and reduced potential for collateral damage relative to conventional photo-activation methods. Such methods are compatible with existing PDT agents along with new classes of light-activated PDT agents. Specifically, the present invention enables improved localization in the photo-activation of any PDT agent with significantly reduced potential for collateral tissue damage compared with that possible using conventional methods.

Where control of optical penetration depth is not critical, un-focused, ultrashort pulsed light may be used to stimulate multi-photon photo-activation of PDT agents present in a relatively large illuminated area or volume. In this case, the extent of PDT agent photo-activation is controlled by varying the location, irradiance and duration of exposure to the light beam.

Where precise control of penetration depth or volume extent of therapeutic application is more critical, focused, ultrashort pulsed light is used to stimulate the multi-photon photo-activation process. In this case, control of beam irradiance, exposure duration, and degree of focusing are used to regulate the extent of PDT agent photo-activation. Furthermore, the high penetration depths achievable with NIR radiation combined with the inherent localization of photo-activation that is possible with focused multi-photon excitation provide a unique means for photo-activating PDT agents in subsurface lesions without damaging overlying or underlying healthy tissues.

Tissue denaturation is a localized, combination photo-chemical and photophysical process resulting from rapid heating of endogenous or exogenous agents. Such heating results from conversion of incident optical energy into thermal energy upon absorption of such optical energy by one or more endogenous or exogenous agents (such as for example blood). Denaturation can result in change of volume of such agents or of surrounding tissues (such as shrinkage or expansion of corneal stem cells), change in physical properties (such as hardness of dental enamels), or initiation of polymerization (such as coagulation of blood). The multi-photon photo-activation methods taught in the present invention, when used to activate responsive agents, allow improved control over the site of such denaturation as a consequence of the decreased loss of activating energy to surrounding tissue when such response is stimulated using ultrashort pulsed excitation. Specifically, the present invention enables improved localization in the photo-activation of responsive agents with significantly reduced potential for collateral tissue damage compared with that possible using conventional methods.

Where control of optical penetration depth is not critical, un-focused, ultrashort pulsed light may be used to stimulate photo-activation of agents present in a relatively large illuminated area. In this case, the extent of agent photo-activation is controlled by varying the location, irradiance and duration of exposure to the light beam.

Where precise control of penetration depth or volume extent of therapeutic application is more critical, focused, ultrashort pulsed light is used to stimulate the photo-activation process. In this case, control of beam irradiance, exposure duration, and degree of focusing are used to regulate the extent of agent photo-activation. Furthermore, the high penetration depths achievable with NIR radiation combined with the inherent localization of photo-activation provide a unique means for photo-activating responsive agents in subsurface zones without damaging overlying or underlying healthy tissues. This feature is useful for various non-invasive therapeutic processes, such as refractive vision correction effected by localized modification of corneal stem cell volume.

Ablation is a localized, photochemical and photophysical process that is initiated by photoionization of endogenous or exogenous agents. When numerous agent molecules contained in a small focal volume are photoionized in an essentially simultaneous manner, violent localized expansion of such agents can occur, resulting in expulsion of material from the focal volume. Such ablative expulsion is useful for various surgical applications, including skin resurfacing and superficial corneal shaping. The multi-photon photo-activation methods taught in the present invention, when used to activate responsive agents, allow improved efficiency in the excitation of such agents along with enhanced control over the site of such ablation. The latter feature is a consequence of the decreased loss of activating energy to surrounding tissue when such response is stimulated using ultrashort pulsed excitation. Specifically, the present invention enables improved localization in the photo-activation of responsive agents with significantly reduced potential for collateral tissue damage compared with that possible using conventional methods.

Specific improvements in ablative efficiency and selectivity relative to that possible using prior methods (such as non-resonant laser-induced breakdown taught by Mourou et al., U.S. Pat. No. 5,656,186) are made possible by the use of wavelength selection methods as taught by the present invention. More specifically, by selection of excitation wavelengths so as to maximize efficiency of excitation based on optimal agent spectral features (such as for example 532 nm for excitation of hemoglobin, 2000 nm or 3000 nm for excitation of water, and 500–800 nm for excitation of melanin), the efficiency of ablation may be increased by as much as 10,000-fold over that possible with prior methods that are based on other ultrashort pulsed photo-activation methods. Further, such enlightened selection of excitation wavelength enables selective activation of specific tissue components. For example, reference to FIG. 10 reveals that multi-photon excitation at 700 nm will afford an approximate 100-fold selectivity enhancement for photo-activation of melanin relative to blood due to differences in absorbance properties for these tissues. Similar enhancements are possible through selective photo-activation of various endogenous or exogenous agents, such as for example tattoo dyes, thereby providing additional means for improving performance of therapeutic processes such as tattoo removal.

Furthermore, the high penetration depths achievable with NIR radiation combined with the inherent localization of photo-activation provide a unique means for photo-activating responsive agents in subsurface zones without damaging overlying or underlying healthy tissues. This feature is useful for various non-invasive therapeutic processes, such as for example refractive vision correction effected by localized ablation of corneal tissue from an inside surface of the cornea.

PREFERRED EMBODIMENTS OF THE PRESENT INVENTION

Figure 11:
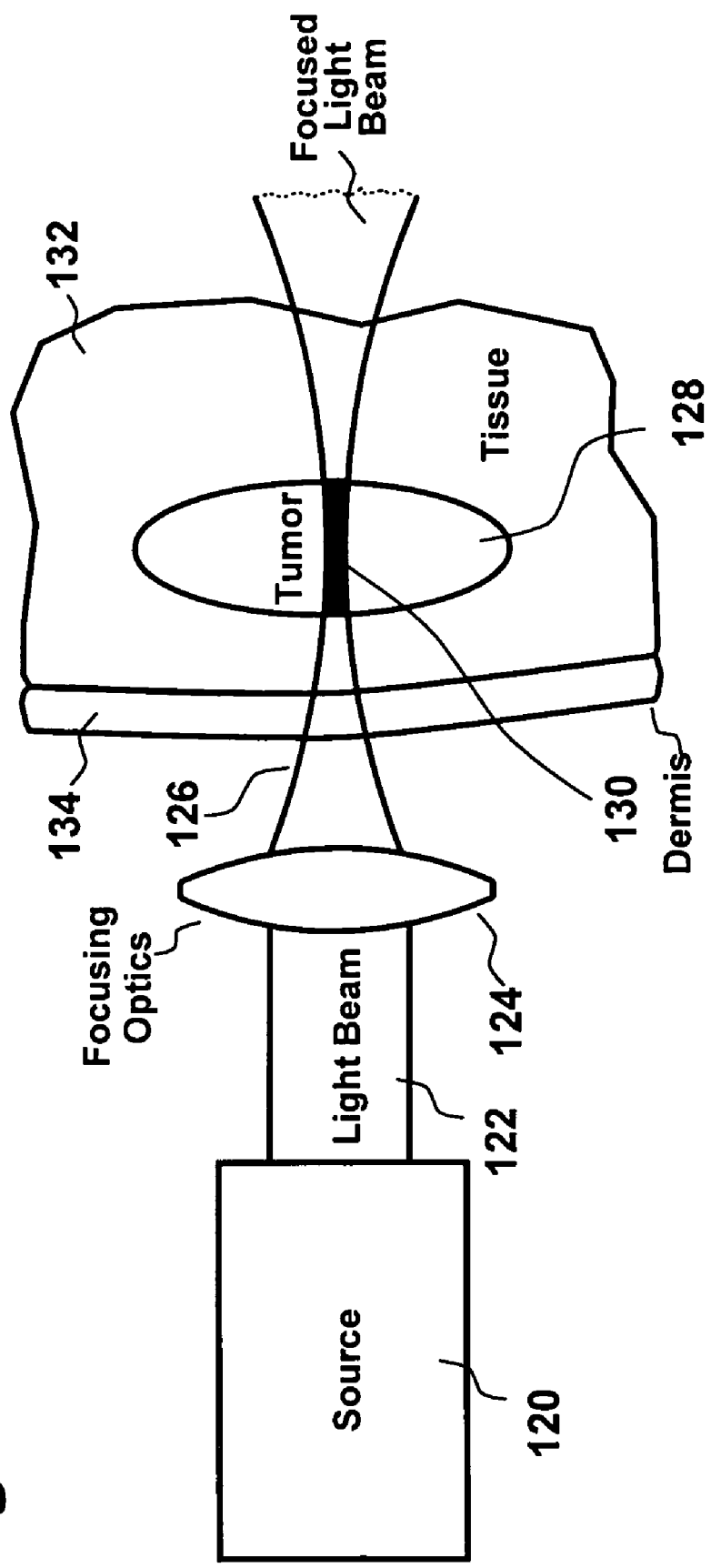
FIG. 11 shows a preferred embodiment of the present invention for selective multi-photon photo-activation of agents present in tissue to be treated.

Hence, it is a preferred embodiment of the present invention to employ the output of a high instantaneous irradiance, ultrashort pulsed source, such as the mode-locked titanium-sapphire laser or the regeneratively amplified titanium:sapphire laser, to induce multi-photon photo-activation of one or more endogenous or exogenous photo-active agents. This preferred embodiment is shown in FIG. 11. The source (120) produces a light beam (122) consisting of a rapid series of ultrashort pulses of optical radiation, typically NIR optical radiation. This light beam (122) is focused using standard optical means, such as reflective or refractive optics (124). The resultant focused light beam (126) is then directed onto tissue to be treated (128), such as a cancerous tumor. Multi-photon photo-activation of the photo-active agent will be substantially limited to the focal zone (130) of the focused light beam (126) due to the high instantaneous irradiance that is only present at such focus. Furthermore, regardless of whether agent is present in surrounding healthy tissue (132) or skin (134), insignificant collateral photo-activation or photodamage will occur outside of the focal zone (130). This is a consequence of the non-linear relationship between instantaneous irradiance and multi-photon excitation, which limits significant excitation to the focal zone (130). Hence, even if the agent is present outside of the focal zone (130), instantaneous irradiances are below that necessary to produce significant photo-activation. This aspect of the preferred embodiment of the present invention is in marked contrast with prior processes, which afforded no practical means for tightly limiting the dimensions of the photo-activation zone along both the areal extent of the beam and its radial path. By scanning the location of the focal zone (130) throughout the volume of the tissue to be treated (128), complete photo-activation of the agent throughout the tissue to be treated (128) can be effected. This scanning action can be produced by changing the position of the focal zone (130) relative to that of the tissue to be treated (128), or by moving the tissue to be treated (128) relative to a stationary location of the focal zone (130). The spatial quality of the focal zone (130) may be improved by pre-expanding the light beam (122), using a beam expander or other device, prior to focusing.

Figure 12:
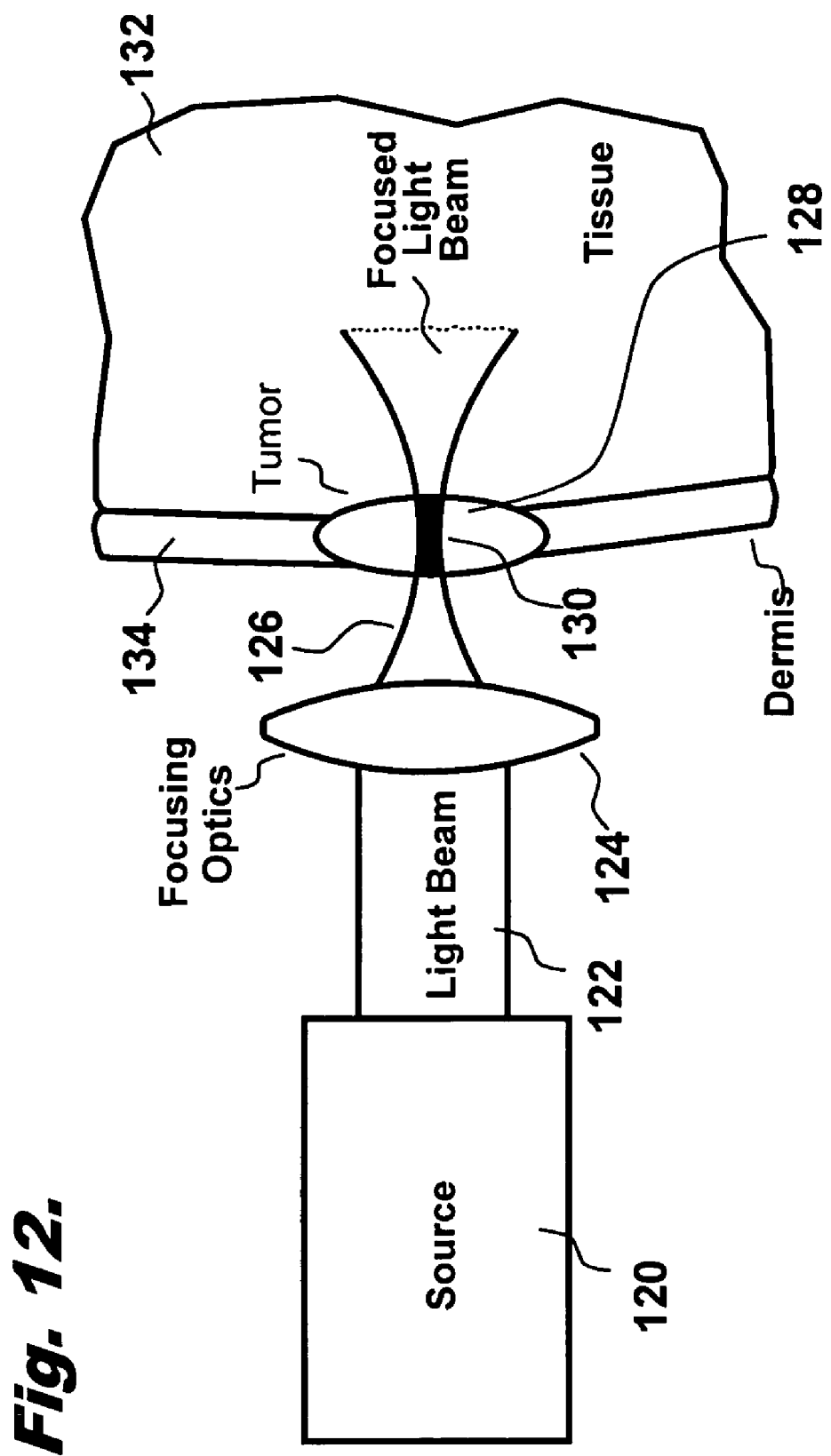
FIG. 12 shows another embodiment for topical therapy using focused light.
Figure 13:
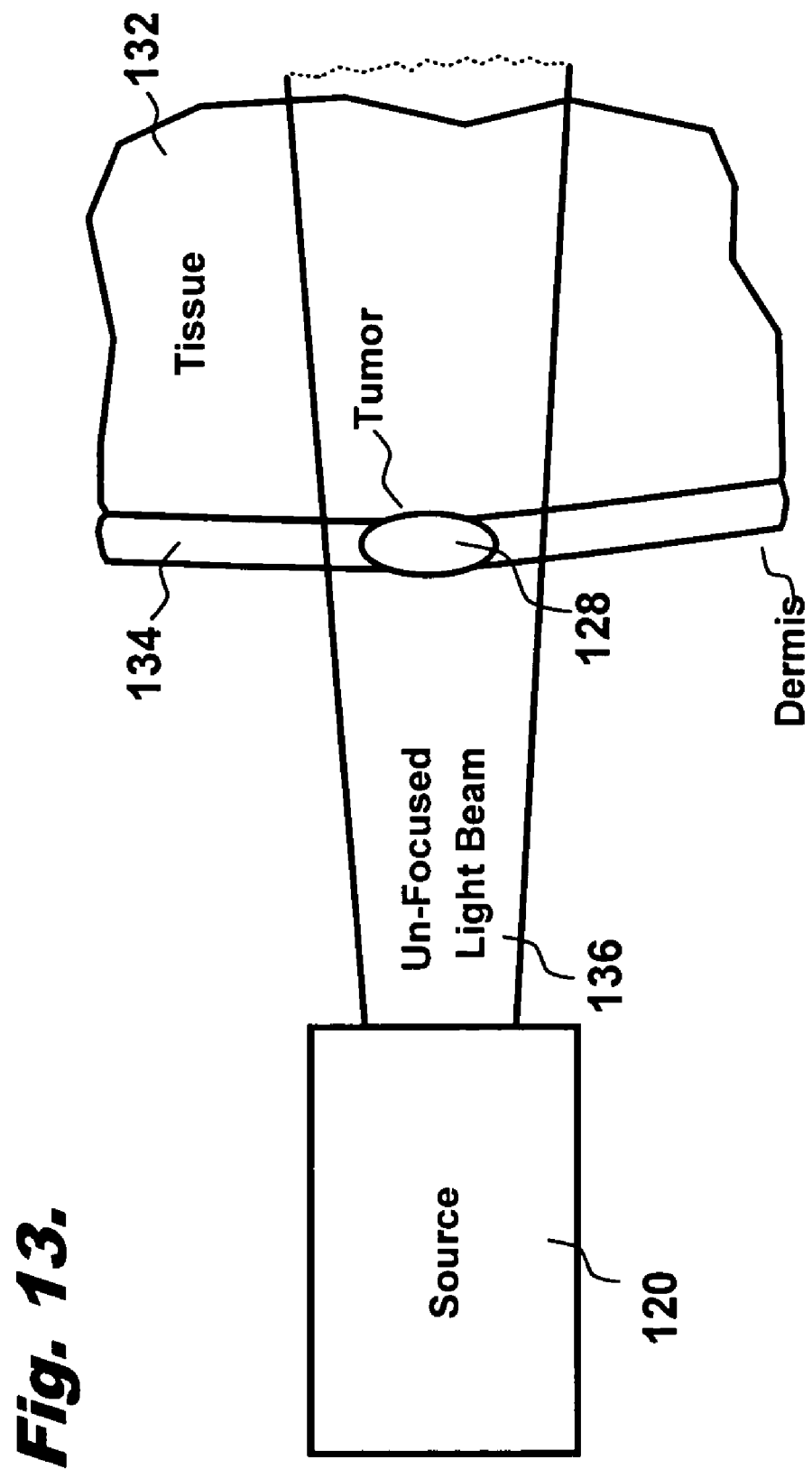
FIG. 13 shows another embodiment for topical therapy using non-focused light.

This multi-photon photo-activation embodiment has several variations for the treatment of topical sites, as shown in FIG. 12 and in FIG. 13. For example, the non-damaging nature of focused NIR light, shown in FIG. 12, or of non-focused NIR light, shown in FIG. 13, allows photo-activation of agents at topical locations without risk to underlying or surrounding tissues.

Focused multi-photon photo-activation of one or more agents for topical therapy, as shown in FIG. 12, is effected when a light beam (122) is focused onto a tissue to be treated (128) using standard optical means, such as reflective or refractive optics (124). In this manner, photo-activation of the agent occurs only at the focal zone (130). The surrounding healthy tissue (132) and skin (134) are unaffected in this process, even if they also contain the agent, since photo-activation is substantially limited to the focal zone (130). As described previously, a scanning action can be used to effect photo-activation of the agent throughout the volume of the tissue to be treated (128).

Non-focused multi-photon photo-activation of one or more agents for topical therapy, as shown in FIG. 13, is effected when an un-focused or expanded light beam (136) from a source (120) is directed onto tissue to be treated (128). This light beam (136) may have a cross sectional area smaller than, equal to, or larger than that of the tissue to be treated (128). If the agent is made to be substantially restricted to the volume of the tissue to be treated (128), for example through controlled application of a PDT agent (such as a topical psoralen cream) or by natural concentration of an endogenous agent (such as melanin), then therapeutic action will be substantially limited to the volume of the tissue to be treated (128). Since the light beam (136) is non-damaging to tissues that do not contain a significant concentration of the agent, damage to surrounding healthy tissue (132) and skin (134) is avoided. This embodiment may be particularly useful when the exact location, size and shape of the tissue to be treated (128) are not known, or when it is otherwise undesirable to precisely control the location of application of the light beam (136), since precise control of the location of the light beam (136) is not critical for successful administration of this therapeutic regime. When non-focused light is used, employment of high peak power excitation sources, such as for example amplified lasers, may be beneficial since such sources will afford high instantaneous irradiance over a large area.

A final related variation of this preferred embodiment for multi-photon photo-activation is shown in FIG. 14, where an un-focused or expanded light beam (136) from a source (120) is directed onto a subsurface tissue to be treated (128). This light beam (136) may have a cross sectional area smaller than, equal to, or larger than that of the tissue to be treated (128). If agent is made to be substantially restricted to the volume of the tissue to be treated (128), for example through controlled application of an exogenous agent or through natural concentration of an endogenous agent, then therapeutic action will be substantially limited to the volume of the tissue to be treated (128). Since the light beam (136) is non-damaging to tissues that do not contain a significant concentration of the agent, damage to surrounding healthy tissue (132) and skin (134) is avoided. This embodiment may also be particularly useful when the exact location, size and shape of the tissue to be treated (128) are not known, or when it is otherwise undesirable to precisely control the location of application of the light beam (136), since precise control of the location of the light beam (136) is not critical for successful administration of this therapeutic regime. As in the previous non-focused embodiment, employment of high peak power excitation sources may be beneficial since such sources will afford high instantaneous irradiance over a large area.

Implication of the Multi-Photon Photo-Activation Method for Standard PDT Agents and for New PDT Agents Standard PDT agents have tissue specificities that in general are based on the combined chemical and physical properties of the agent and the tissue, such as a cancerous lesion. For example, various psoralen derivatives;
various porphyrin and hematoporphyrin derivatives;
various chlorin derivatives;

various phthalocyanine derivatives;
various rhodamine derivatives;
various coumarin derivatives;
various benzophenoxazine derivatives;
chlorpromazine and its derivatives;
various chlorophyll and bacteriochlorophyll derivatives;
pheophorbide a [Pheo a]; merocyanine 540 [MC 540]; Vitamin D; 5-amino-laevulinic acid [ALA]; photosan; pheophorbide-a [Ph-a]; phenoxazine Nile blue derivatives (including various phenoxazine dyes);
various charge transfer and radiative transfer agents; and
numerous other photo-active or photosensitizing agents, will in general become accumulated either at or near a point of application or semi-selectively within a specific tissue due to differences in the physical or chemical properties of the tissue which lead to partitioning of the PDT agent into the tissue.

These agents are conventionally activated using single-photon or sequential two-photon activation methods that promote one or more photo-chemical or photo-physical processes, including but not limited to bond formation or cleavage, adduct formation, cross-linking, free radical production, singlet oxygen production, generation of toxic substances, and energy transfer. The conventional methods used for activation of such agents afford minimal selectivity in the extent or depth of activation, and are normally limited to use with superficial tissues or lesions.

It will be clear from the foregoing discussion, preferred embodiments and supporting data that the present invention taught in this application is applicable to all of these listed agents and photosensitizers as well as other PDT agents and photosensitizers not specifically listed. Specifically, all of these agents will be responsive to multi-photon excitation at wavelengths longer than those used for single-photon excitation, and once excited, will exhibit behaviors equivalent to those resulting from single-photon excitation. Furthermore, the improvements over control of point of application and in reduction of collateral damage taught herein afford additional specific advantages to the use of multi-photon excitation in place of conventional single-photon or sequential two-photon activation. These include enhanced depth of penetration, enhanced spatial control over point of application, and reduced side-effects from PDT treatment.

Many new PDT agents are being developed that are susceptible to direct single-photon activation in the NIR. The intention with these agents is reduction of side-effects and other limitations associated with conventional UV or visible photo-activation. Examples of such agents include PHOTOFRIN®, benzoporphyrin derivative mono-acid, SnET2, Lutex, and other related agents that can be photo-activated using single-photon excitation at wavelengths greater than 500 nm. The present invention taught in this application has specific advantages with these classes of agents as well. Specifically, use of multi-photon photo-activation at wavelengths in the 500 to 4000 nm spectral band can afford considerably greater depth of penetration than that possible with single-photon activation because of greatly reduced tissue absorbance and scatter in this band in comparison to shorter wavelength light necessary for linear excitation. Additionally, the spatial localization advantages of multi-photon photo-activation taught herein will afford improved control over the point of application of such therapy in comparison with single-photon activation methods.

It will be clear that while the foregoing disclosure has primarily focused on example therapeutic applications using multi-photon excitation of agents with ultrashort pulsed NIR optical radiation produced by mode-locked titanium:sapphire lasers, the present invention is not limited to such excitation nor to such narrowly defined optical sources. In fact, aspects of the present invention are applicable when optical excitation is effected using linear or other non-linear methods. For example, various other optical sources are applicable, alone or in combination, such as continuous wave and pulsed lamps, diode light sources, semiconductor lasers; other types of gas, dye, and solid-state continuous, pulsed, or mode-locked lasers, including: argon ion lasers; krypton ion lasers; helium-neon lasers; helium-cadmium lasers; ruby lasers; Nd:YAG, Nd:YLF, Nd:YAP, Nd:YVO4, Nd:Glass, and Nd:CrGsGG lasers; Cr:LiSF lasers; Er:YAG lasers; F-center lasers; Ho:YAF and Ho:YLF lasers; copper vapor lasers; nitrogen lasers; optical parametric oscillators, amplifiers and generators; regeneratively amplified lasers; chirped-pulse amplified lasers; and sunlight.

Further, while the foregoing disclosure has focused on therapeutic applications for in vivo treatment of disease in plant and animal tissue, it will also be clear that the present invention has additional utility whenever selective modification of a responsive target agent is desirable. Specifically, application of the present invention in the control of manufacture or purification of materials of biological origin or contaminated with materials of biological origin are covered within the scope of the present invention. As an example, selective treatment or purification of biological fluids, such as blood or plasma, based on the targeted interaction of a photosensitizable agent with a target entity, such as the HIV virus, is contemplated. This approach could serve a therapeutic role in the treatment of HIV infection and as a protective measure for the prevention of transmission of HIV through blood transfusions. As a second example, manufacture of extremely pure biological products, such as cell cultures, wherein a heterogeneous parent culture is purified by selective destruction of a targeted contaminant agent, is contemplated. As a third example, production of genetically induced biological products based on selective stimulation of one or more specific gene sequences in targeted biological agents is contemplated.

In addition to various biological applications, it will also be clear that numerous non-biological applications will be made possible or their efficiencies dramatically improved by utilization of the present invention, including the manufacture of high purity or commodity materials, especially where the special properties of non-linear optical excitation are important. For example, production or processing of specialty chiral chemicals, pigments, paints, polymeric materials and other industrial or commercial agents can be improved through application of aspects of the present invention. Specifically, the unique selection rules, selectivity advantages, and localization of activation, offer advantages in many materials production or processing steps. In fact, these examples make it clear that the present invention actually constitutes a general materials processing paradigm, wherein the special properties of non-linear optical excitation are used on biological or non-biological materials to effect specific improvements in the selective conversion of starting materials into products, regardless of whether the transformation is from tumor to necrotic tissue or from one molecular agent to another.

Also, while the foregoing example has focused primarily on therapeutic issues pertaining to humans, direct applicability to microbial, plant and animal specimens will also be obvious. For example, treatment of disease in livestock, breeding stock, or in other veterinary capacities is envisioned. Also, use of the method for treatment or as a means for achieving selectivity in microbial or cell cultures is envisioned. For example, portions of the present invention will be useful for purification of heterogeneous cell cultures and in the expression of cell function in vitro. Hence, the present invention has application to the fields of genetic engineering, animal husbandry, reproductive therapy, cloning, and many others.

The multi-photon photoactivation of the prsent invention could also be used to activate diagnostic imaging agents.

It will be understood that each of the elements described above, or two or more together, may also find useful application in other types of constructions or applications differing from the types described above.

While the present invention has been illustrated and described as embodied in general methods for improved selectivity in photo-activation of therapeutic agents, it is not intended to be limited to the details shown, since it will be understood that various omissions, modifications, substitutions and changes in the forms and details of the method illustrated and in its operation can be made by those skilled in the art without departing in any way from the spirit of the present invention.

This description has been offered for illustrative purposes only and is not intended to limit the invention of this application, which is defined in the claims below.

What is claimed as new and desired to be protected by Letters Patent is set forth in the appended claims:

1. A method for the treatment of a particular volume of plant or animal tissue, the method comprising the steps of:
   (a) treating the plant or animal tissue with at least one photo-active agent, wherein the particular volume of the plant or animal tissue retains at least a portion of the at least one photo-active agent; and
   (b) treating the particular volume of the plant or animal tissue with light to promote a multi-photon photoactivation of at least one of said at least one photo-active agent retained in the particular volume of the plant or animal tissue, wherein the at least one excited photo-active agent becomes photo-activated in the particular volume of the plant or animal tissue.

2. The method of claim 1 wherein the light to promote said multi-photon photoactivation is a laser light produced by a laser.

3. The method of claim 2 wherein the laser light comprises a train of one or more ultrashort pulses.

4. The method of claim 3 wherein each of said one or more pulses has a duration of at most approximately 10 ps.

5. The method of claim 2 including operating the laser to produce light at a wavelength between approximately 500 nm to 4000 nm.

6. The method of claim 1 wherein said light is at a wavelength between approximately 500 nm to 4000 nm.

7. The method of claim 1 wherein the light to promote said multi-photon photoactivation is a focused beam of light.

8. The method of claim 7 wherein the focused beam of light is focused laser light.

9. The method of claim 1 wherein said step of treating the particular volume of the plant or animal tissue includes positioning a focus of a beam of light over a range of positions so that a focal plane of the light beam occurs at a site located between a surface of the tissue and a point substantially beyond the tissue surface, whereby said step of treating the particular volume of the plant or animal tissue may extend to penetrate deep within the tissue.

10. The method of claim 9 further including vying, while the beam of light is extant, the radial position of the focal plane within the tissue, thereby to photoactivate the at least one photo-active agent at a multiplicity of positions between the tissue surface and a position located substantially beyond the tissue surface.

11. The method of claim 1 wherein said at least one photo-active agent becomes photoactivated in said particular volume at a controllable position substantially beyond a tissue surface.

12. The method of claim 11 wherein said treating step includes directing a laser light to said particular volume.

13. The method of claim 12 wherein said treating step includes directing a pulsed laser light to said particular volume.

14. The method of claim 13 wherein said laser is pulsed to produce pulses of at most approximately 10 ps.

15. The method of claim 1 wherein said multi-photon photoactivation includes an essentially simultaneous interaction of at least two photons with said agent so as to produce a photo-activated agent.

16. The method of claim 1 wherein said agent is selected from the group comprising psoralen derivatives; porphyrin and hematoporphyrin derivatives; chlorin derivatives; phthalocyanine derivatives; rhodamine derivatives; coumarin derivatives; benzophenoxazine derivatives; chlorpromazine and chlorpromazine derivatives; chlorophyll and bacteriochlorophyll derivatives; pheophorbide a (Pheo a); merocyanine 540 (MC 540); Vitamin D; 5-amino-laevulinic acid (ALA); photosan; pheophorbide-a (Ph-a); phenoxazine Nile blue derivatives including various phenoxazine dyes; PHOTOFRIN; benzoporphyrin derivative mono-acid; SnET2; and Lutex.

17. The method of claim 1 wherein said multi-photon photoactivation is a degenerate process.

18. The method of claim 1 wherein said method for treatment is for photodynamic treatment of disease.

19. The method of claim 1 wherein said method for treatment is for selective tissue denaturation.

20. The method of claim 1 wherein said method for treatment is for laser surgery.

21. The method of claim 1 wherein said method for treatment is for tattoo removal.

22. The method of claim 1 wherein said multi-photon photoactivation involves n photons, and wherein n equals 2 or more photons and can be varied so as to optimize the volume of tissue in which said agent is photoactivated.

23. The method of claim 1 fixer comprising the step of controlling the photo-activation by varying the location, irradiance and duration of said light.

24. The method of claim 3 further comprising the step of varying the pulse energy of said one or more ultrashort pulses to achieve a desired therapeutic process.

25. The method of claim 24 wherein said pulse energy is set so that said desired therapeutic process is substantially a photophysical process.

26. The method of claim 24 wherein said pulse energy is set so that said desired therapeutic process is substantially a photochemical process.

27. The method of claim 1 wherein said multi-photon activation results in electronic excitation of said at least one photo-active agent to a higher quantum mechanically allowed state.

28. The method of claim 1 wherein said multi-photon activation results in vibrational excitation of said at least one photo-active agent to a higher quantum mechanically allowed state.

29. The method of claim 1 wherein said multi-photon activation results in photoionization of said at least one photo-active agent.

30. The method of claim 1 wherein the light to promote said multi-photon excitation of the photo-active agent is an unfocused beam of light.

31. The method of claim 30 wherein said particular volume of tissue is located substantially at the tissue surface.

32. The method of claim 30 wherein said particular volume of tissue is located substantially below the tissue surface.

33. The method of claim 30 further comprising the step of substantially restricting said agent to the particular volume of tissue to be treated.

34. The method of claim 1 further comprising the step of selecting a wavelength for said light to promote said multi-photon activation so as to optimize the efficiency and selectivity of photo-activation of said at least one photoactive agent within said volume of tissue.

35. The method of claim 9 further comprising the step of controlling the fineness of the focus of said beam via beam expansion and subsequent focusing of said beam of light prior to said treating with light.

36. A method for producing at least one photoactivated agent in a particular volume of a material, the method comprising treating the particular volume of the material with light to promote a multi-photon excitation of at least one photo-active agent contained in the particular volume of the material, wherein the at least one photo-active agent becomes a photo-activated agent in the particular volume of the material.

37. The method of claim 36 wherein the material is pretreated with at least one photo-active agent such that the material retains at least a portion of the at least one photo-active agent at the time that the particular volume of the material is treated with light sufficient to promote said multi-photon excitation of at least one of said at least one photo-active agent.

38. The method of claim 36 wherein the material is selected from the group consisting of plant tissue and animal tissue.

39. The method of claim 38 wherein said at least one photo-active agent becomes photoactivated in said particular volume at a controllable position.

40. The method of claim 38 wherein said agent is an exogenous agent.

41. The method of claim 40 wherein said exogenous agent is selected from the group comprising psoralen derivatives; porphyrin and hematoporphyrin derivatives; chlorin derivatives; phthalocyanine derivatives; rhodamine derivatives; coumarin derivatives; benzophenoxazine derivatives; chlorpromazine and chlorpromazine derivatives; chlorophyll and bacteriochlorophyll derivatives; pheophorbide a (Pheo a); merocyanine 540 (MC 540); Vitamin D; 5-amino-laevunlic acid (ALA); photosan; pheophorbide-a (Ph-a); phenoxazine Nile blue derivatives including various phenoxazine dyes; PHOTOFRIN; benzoporphyrin derivative mono-acid; SnET2; and Lutex.

42. The method of claim 38 wherein said agent is an endogenous agent.

43. The method of claim 42 wherein said endogenous agent is selected from the group comprising proteins, natural chromophoric agents including melanin, hemoglobin and carotenes, water, collagen and tattoo dyes.

44. The method of claim 36 wherein the light to promote said multi-photon excitation of the photo-active agent is laser light produced by a laser.

45. The method of claim 44 wherein the laser light comprises a train of one or more ultrashort pulses.

46. The method of claim 45 wherein each of said one or more pulses has a duration of at most approximately 10 ps.

47. The method of claim 44 including operating said laser to produce light at a wavelength between approximately 500 nm to 4000 nm.

48. The method of claim 36 wherein said light is at a wavelength between approximately 500 nm to 4000 nm.

49. The method of claim 36 wherein the light to promote said multi-photon excitation of the photo-active agent is a focused beam of light.

50. The method of claim 49 wherein the focused beam of light is laser light.

51. The method of claim 50 wherein the fineness of focus of said beam of laser light is controlled via beam expansion and subsequent focusing of said beam of light prior to said treating with light.

52. The method of claim 36 wherein said step of treating the particular volume of material includes positioning a focus of a beam of light over a range of positions so that a focal plane of the light beam occurs at a site located between a surface of the material and a point substantially beyond the material surface, whereby said step of treating the particular volume of material may extend to penetrate deep within the material.

53. The method of claim 52 wherein said at least one photo-active agent becomes photoactivated in said particular volume at a controllable position substantially beyond a tissue surface.

54. The method of claim 36 wherein said treating step includes directing a laser light to said particular volume.

55. The method of claim 36 wherein said treating step includes directing a pulsed laser light to said particular volume.

56. The method of claim 55 wherein said laser is pulsed to produce pulses having a duration of at most approximately 10 ps.

57. The method of claim 52 further including varying, while the beam of light is extant, the radial position of the focal plane within the material, thereby to photoactivate the at least one photo-active agent at a multiplicity of positions between the material surface and a position located substantially beyond the material surface.

58. The method of claim 36 wherein said multi-photon photoactivation includes an essentially simultaneous interaction of at least two photons with said agent so as to produce a photoactivated agent.

59. The method of claim 36 wherein said multi-photon photoactivation is a degenerate process.

60. The method of claim 38 wherein said method for treatment is for photodynamic treatment of disease.

61. The method of claim 38 wherein said method for treatment is for selective tissue denaturation.

62. The method of claim 38 wherein said method for treatment is for laser surgery.

63. The method of claim 38 wherein said method for treatment is for tattoo removal.

64. The method of claim 36 wherein said multi-photon photoactivation involves n photons, and wherein n equals 2 or more photons and can be varied so as to optimize the volume of material in which said agent is photoactivated.

65. The method of claim 36 further comprising the step of controlling the photo-activation by varying the location, irradiance and duration of said light.

66. The method of claim 45 further comprising the step of varying the pulse energy of said one or more ultrashort pulses to achieve a desired therapeutic process.

67. The method of claim 66 wherein said pulse energy is set so that said desired therapeutic process is substantially a photophysical process.

68. The method of claim 66 wherein said pulse energy is set so that said desired therapeutic process is substantially a photochemical process.

69. The method of claim 36 wherein said multi-photon activation results in electronic excitation of said at least one photo-active agent to a higher quantum mechanically allowed state.

70. The method of claim 36 wherein said multi-photon activation results in vibrational excitation of said at least one photo-active agent to a higher quantum mechanically allowed state.

71. The method of claim 36 wherein said multi-photon activation results in photoionization of said at least one photo-active agent.

72. The method of claim 36 wherein the light to promote said multi-photon excitation of the photo-active agent is an unfocused beam of light.

73. The method of claim 72 wherein said particular volume of material is located substantially at a surface of the material.

74. The method of claim 72 wherein said particular volume of tissue is located substantially below a surface of the material.

75. The method of claim 72 further comprising the step of substantially restricting said agent to the particular volume of material tissue to be treated.

76. The method of claim 36 further comprising the step of selecting a wavelength for said light to promote said multi-photon excitation so as to optimize the efficiency and selectivity of photo-activation of said at least one photoactive agent within said volume of material.

77. A method for the medical treatment of a particular volume of tissue wherein the tissue includes at least one photo-active agent, the method comprising the steps of:
    directing light to specific regions of interest within the tissue, including regions substantially below a tissue surface, said light being selected to penetrate the tissue and to promote multi-photon excitation substantially only at a focal zone;
    controlling the location of said focal zone over a range of depths within said tissue; and
    using multi-photon excitation, photoactivating at least one of said at least one agent over said range of depths within said tissue, thereby producing at least one photo-activated agent substantially only at the focal zone.

78. The method of claim 77 wherein said directing step includes directing a laser light produced by a laser to said particular volume.

79. The method of claim 77 wherein said directing step includes directing one or more ultrashort laser pulses to said particular volume.

80. The method of claim 79 wherein said laser is operated to produce pulses, each of said pulses having a duration of at most approximately 10 ps.

81. The method of claim 77 wherein the tissue is pretreated with at least one photo-active agent such that the tissue retains at least a portion of said at least one photo-active agent at the time that the particular volume of the tissue is treated with light sufficient to promote a multi-photon excitation of at least one of said at least one photo-active agent.

82. The method of claim 77 wherein said agent is an endogenous agent.

83. The method of claim 82 wherein said endogenous agent is selected from the group comprising proteins, natural chromophoric agents including melanin, hemoglobin and carotenes, water, collagen and tattoo dyes.

84. The method of claim 77 wherein said agent is an erogenous agent.

85. The method of claim 84 wherein said erogenous agent is selected from the group comprising psoralen derivatives; porphyrin and hematoporphyrin derivatives; chlorin derivatives; phthalocyanine derivatives; rhodamine derivatives; coumarin derivatives; benzophenoxazine derivatives; chlorpromazine and chlorpromazine derivatives; chlorophyll and bacteriochlorophyll derivatives; pheophorbide a (Pheo a); merocyanine 540 (MC 540); Vitamin D; 5-amino-laevulinic acid (ALA); photosan; pheophorbide-a (Ph-a); phenoxazine Nile blue derivatives including various phenoxazine dyes; PHOTOFRIN; benzoporphyrin derivative mono-acid; SnET2; and Lutex.

86. The method of claim 77 wherein the light to promote said multi-photon excitation of the photo-active agent is laser light having a wavelength from approximately 500 nm to 4000 µm.

87. The method of claim 77 wherein the light to promote said multi-photon excitation of the photo-active agent is a focused beam of light.

88. The method of claim 87 wherein the focused beam of light is laser light.

89. The method of claim 77 wherein the light to promote said multi-photon excitation of the photo-active agent is an unfocused beam of light.

90. The method of claim 89 wherein said regions of interest are located substantially at the tissue surface.

91. The method of claim 89 wherein said regions of interest are located substantially below the tissue surface.

92. The method of claim 89 further comprising the step of substantially restricting said agent to the particular volume of tissue to be treated.

93. The method of claim 77 wherein said step of treating the particular volume of the plant or animal tissue includes positioning a focus of a beam of light over a range of positions so that a focal plane of the light beam occurs at a site located between a surface of the tissue and a point substantially beyond the tissue surface, whereby said step of treating the particular volume of the plant or animal tissue may extend to penetrate deep within the tissue.

94. The method of claim 77 wherein said at least one photo-active agent becomes photoactivated in said particular volume at a controllable position substantially beyond a tissue surface.

95. The method of claim 77 further including varying, while the beam of light is extant, the radial position of the focal plane with the tissue, thereby to photoactivate the at least one photo-active agent at a multiplicity of positions between the tissue surface and a position located substantially beyond the tissue surface.

96. The method of claim 77 wherein said multi-photon photoactivation includes an essentially simultaneous interaction of at least two photons with said agent so as to produce a photo-activated agent.

97. The method of claim 77 wherein said multi-photon photoactivation is a degenerate process.

98. The method of claim 77 wherein said method for treatment is for photodynamic treatment of disease.

99. The method of claim 77 wherein said method for treatment is for selective tissue denaturation.

100. The method of claim 77 wherein said method for treatment is for laser surgery.

101. The method of claim 77 wherein said method for treatment is for tattoo removal.

102. The method of claim 77 wherein said multi-photon photoactivation involves n photons, and wherein n equals 2 or more photons and can be varied so as to optimize the volume of tissue in which said agent is photoactivated.

103. The method of claim 77 further comprising the step of controlling the photo-activation by varying the location, irradiance and duration of said light.

104. The method of claim 79 further comprising the step of varying the pulse energy of said one or more ultrashort pulses to achieve a desired therapeutic process.

105. The method of claim 104 wherein said pulse energy is set so that said desired therapeutic process is substantially a photophysical process.

106. The method of claim 104 wherein said pulse energy is set so that said desired therapeutic process is substantially a photochemical process.

107. The method of claim 77 wherein said multi-photon activation results in electronic excitation of said at least one photo-active agent to a higher quantum mechanically allowed state.

108. The method of claim 77 wherein said multi-photon activation results in vibrational excitation of said at least one photo-active agent to a higher quantum mechanically allowed state.

109. The method of claim 77 wherein said multi-photon activation results in photoionization of said at least one photo-active agent.

110. The method of claim 77 wherein said photoactivating step includes using energy of a first photon to excite at least one of said at least one agent to a transient virtual level between an initial state and an excited state and using energy of at least a second photon to excite said agent to a quantum mechanically allowed excited state before said agent makes a transition back to the initial state.

111. The method of claim 77 further comprising the step of selecting a wavelength for said light to promote said multi-photon activation so as to optimize the efficiency and selectivity of photo-activation of said at least one photoactive agent within said volume of tissue.

112. The method of claim 77 wherein the fineness of said focal zone is controlled via beam expansion and subsequent focusing of said beam of light prior to said directing step.

113. A method for the treatment of a particular volume of plant or animal tissue, the tissue including at least one photoactive agent in the particular volume, the method comprising:

illuminating said particular volume of tissue to cause multi-photon excitation of at least one of said at least one photo-active agent, wherein said at least one photo-active agent at a site of the multi-photon excitation is firstly excited to a transient virtual state and secondly excited to a quantum mechanically allowed excited state and wherein the at least one excited photo-active agent becomes photo-activated in the particular volume.

114. The method of claim 113 including the treatment of a particular volume of plant or animal tissue located substantially below a tissue surface.

115. The method of claim 114 wherein said illumination with light and said transient virtual state occurs substantially only at said particular volume, despite the passage of light through other tissue portions between said surface and said particular volume.

116. The method of claim 115 further comprising the step of selecting a wavelength for said light to promote said multi-photon activation so as to optimize the efficiency and selectivity of photo-activation of said at least one photoactive agent within said volume of tissue.

117. The method of claim 115 further including varying the position where multi-photon excitation occurs over a range of depths below the tissue surface.

118. The method of claim 113 wherein said illuminating step includes directing a laser beam produced by a laser to said particular volume.

119. The method of claim 113 wherein said illuminating step includes directing an ultrashort pulsed laser beam having one or more pulses of a duration of at most approximately 10 ps to said particular volume.

120. The method of claim 119 wherein an individual photon provided by said pulsed laser beam has insufficient energy to directly excite the agent from a ground state to an excited electronic state.

121. The method of claim 113 wherein said multi-photon photoactivation is a degenerate process.

122. The method of claim 113 wherein said multi-photon photoactivation involves n photons, and wherein n equals 2 or more photons and can be varied so as to optimize the volume of tissue in which said agent is photoactivated.

123. The method of claim 113 including treatment of a particular volume of plant or animal tissue located substantially at a tissue surface.

* * * * *